US012781162B2

(12) United States Patent
Coelho et al.

(10) Patent No.: US 12,781,162 B2
(45) Date of Patent: Nov. 3, 2026

(54) GLUTATHIONE-RICH YEAST AND ITS USE FOR PRESERVING WINES

(71) Applicants: Danstar Ferment AG, Zug (CH); Universite de Bourgogne, Dijon (FR)

(72) Inventors: Christian Coelho, Entraigues (FR); Florian Bahut, Dijon (FR); Maria Nikolantonaki, Dijon (FR); Regis D. Gougeon, Dijon (FR); Nathalie Sieczkowski, Blagnac (FR); Caroline Wilde, Montreal (CA); Corinne Cluis, Montreal (CA)

(73) Assignees: Danstar Ferment AG, Zug (CH); Universite de Bourgogne, Dijon (FR)

( * ) Notice: Subject to any disclaimer, the term of this patent is extended or adjusted under 35 U.S.C. 154(b) by 1241 days.

(21) Appl. No.: 17/434,791

(22) PCT Filed: Mar. 2, 2020

(86) PCT No.: PCT/EP2020/055460
§ 371 (c)(1),
(2) Date: Jan. 31, 2022

(87) PCT Pub. No.: WO2020/178250
PCT Pub. Date: Sep. 10, 2020

(65) Prior Publication Data

US 2023/0124937 A1 Apr. 20, 2023

(30) Foreign Application Priority Data

Mar. 1, 2019 (EP) .................................... 19290014

(51) Int. Cl.
*C12G 1/022* (2006.01)
*C12N 1/185* (2026.01)
*C12R 1/865* (2006.01)

(52) U.S. Cl.
CPC ........... *C12G 1/0203* (2013.01); *C12N 1/185* (2021.05); *C12R 2001/865* (2021.05)

(58) Field of Classification Search
CPC ...... C12N 1/185; C12N 1/18; C12R 2001/865
See application file for complete search history.

(56) References Cited

U.S. PATENT DOCUMENTS 8,268,372 B2 9/2012 Ortiz-Julien

FOREIGN PATENT DOCUMENTS

| | | | |
|---|---|---|---|
| CN | 1535255 | A | 10/2004 |
| CN | 101255454 | A | 9/2008 |
| CN | 104673576 | A | 6/2015 |
| CN | 104962485 | A | 7/2015 |
| CN | 105255748 | A | 1/2016 |
| EP | 1706478 | B1 | 12/2008 |
| WO | 02/70436 | A2 | 9/2002 |

OTHER PUBLICATIONS

CN 104962485 A. Machine Translation. Published Oct. 7, 2015. (Year: 2015).*

Duina, AA et al. Budding yeast for budding geneticists: a primer on the *Saccharomyces cerevisiae* model system. Genetics. 2014. 197: 33-48. (Year: 2014).*

Scettri, A et al. NMR sugar-profile in genuine grape must. Food Chemistry. 2024. 451: 139374. 8 pages. (Year: 2024).*

Jolly, NP et al. Not your ordinary yeast: non-*Saccharomyces* yeasts in wine production uncovered. FEMS Yeast Research. 2014. 14: 215-237. (Year: 2014).*

Alfafara et al., "Effect of amino acids on glutathione production by *Saccharomyces cerevisiae*", Appl. Microbiol. Biotechnol. vol. 36, (1992), pp. 538-540.

Alfafara, C., et al., "Cysteine addition strategy for maximum glutathione production in fed-batch culture of *Saccharomyces cerevisiae*", Applied Microbiology and Biotechnology, 37: 141-146 (1992).

Allen, J., et al., "High-throughput classification of yeast mutants for functional genomics using metabolic footprinting", Nature Biotechnology, 21(6): 692-696 (2003).

Brauer, M.J., et al., "Conservation of the metabolomic response to starvation across two divergent microbes", PNAS, 103(51): 19302-19307 (2006).

Brockman, S.A., et al., "Van Krevelen diagram visualization of high resolution-mass spectrometry metabolomics data with OpenVanKrevelen", Metabolomics, 14: 48, pp. 1-5 (2018).

Chertov, O., et al., "Organic solvent extraction of proteins and peptides from serum as an effective sample preparation for detection and identification of biomarkers by mass spectrometry", Proteomics, 4: 1195-1203 (2004).

Coelho, C., et al., "Asymmetrical flow field-flow fractionation of white wine chromophoric colloidal matter", Anal. Bioanal. Chem., 409: 2757-2766 (2017).

(Continued)

*Primary Examiner* — David W Berke-Schlessel
*Assistant Examiner* — Susan E. Fernandez
(74) *Attorney, Agent, or Firm* — Smith, Gambrell & Russell, LLP; Matthew P. Warenzak

(57) ABSTRACT

The present disclosure concerns a method for the prevention of defective ageing white wines, wherein, during the preparation of said wine, yeast previously rich in glutathione is introduced into the must at the beginning of, during or after the alcoholic fermentation step, the yeast is a *Saccharomyces cerevisiae* strain deposited at Institut Pasteur, on 20 Feb. 2019 under accession number CNCM 1-5404. The present disclosure also concerns glutathione-rich *Saccharomyces cerevisiae* strain deposited at Institut Pasteur, on 20 Feb. 2019 under accession number CNCM 1-5404 as well as processes using the strain in active or inactivated forms for preserving wine. The present disclosure also concerns a glutathione-rich inactivated dry yeast comprising a first dipeptide having the formula C12H25N303 with a molecular weight of 259.3458 g/mole; and a second dipeptide having the formula C12H25N503 with a molecular weight of 287.3593 g/mole, as well as processes using the inactivated dry yeast for preserving wine.

18 Claims, 11 Drawing Sheets

(56) References Cited

OTHER PUBLICATIONS

Dikicioglu, D., et al., "Short- and long-term dynamic responses of the metabolic network and gene expression in yeast to a transient change in the nutrient environment", Mol. BioSyst., 9: 1760-1774 (2012).
Dubourdieu et al., "The role of glutathione on the aromatic evolution of dry white wine", Vinidea Net wine Internet Technical Journal, 02 2004, No. 2, pp. 1-9 (English Translation).
Dubourdieu, D., et al., "Role du glutathion sur l'évolution aromatique des vins blancs secs", Wine Internet Technical Journal, 17: 1-10 (2003).
Elias, R.J., et al., "Antioxidant Activity of Proteins and Peptides", Crit. Reviews in Food Sci. and Nutrition, 430-441 (2008).
Gabrielli et al., "Additions of glutathione or specific glutathione-rich dry inactivated yeast preparation (DYP) to sauvignon blanc must : effect on wine chemical and sensory composition", S. Afr. J. Enol. Vitic., vol. 38, No. 1, Jan. 1, 2017, pp. 18-28.
Gachons et al., Influence of water and nitrogen deficit on fruit ripening and aroma potential of *Vitis vinifera* L cv Sauvignon blanc in field conditions, Journal of the Science of Food and Agriculture, vol. 85, Issue 1, 2005, pp. 73-85.
Gougeon, R.D., et al., "The chemodiversity of wines can reveal a metabologeography expression of cooperage oak wood", PNAS, 106(23): 9174-9179 (2009).
He, M., "Pipecolic acid in microbes: biosynthetic routes and enzymes", J. ind. Microbiol. Biotech., 33: 401-407 (2006).
International Preliminary Report on Patentability received for PCT Patent Application No. PCT/EP2020/055460, mailed on Sep. 16, 2021, 9 pages.
International Search Report and Written Opinion received for PCT Patent Application No. PCT/EP2020/055460, mailed on Jun. 23, 2020, 14 pages.
Kim, S., et al., "Graphical Method for Analysis of Ultrahigh-Resolution Broadband Mass Spectra of Natural Organic Matter, the Van Krevelen Diagram", Analytical Chemistry, 75(20): 5336-5344 (2003).
Kritzinger, E.C., et al., "Role of Glutathione in Winemaking: A Review," Journal of Agricultural and Food Chemistry, vol. 61, No. 2, Dec. 2012, pp. 269-277.
Li, Y., et al., "Glutathione: a review on biotechnological production", Appl. Microbiol. Biotech., 66: 233-242 (2004).
Liu, Y., et al., "Digging into the low molecular weight peptidome with the OligoNet web server", Scientific Reports, 7: 11692 (2017).
Liu, Y., et al., "New molecular evidence of wine yeast-bacteria interaction unraveled by non-targeted exometabolomic profiling", Metabolomics, 12: 69, pp. 1-16 (2016).
Liu, Y., et al., "Wine microbiome, a dynamic world of microbial interactions", Crit. Reviews in Food Sci. and Nutrition, 1-87 (2017).
Moutounet, M., et al, "The Measurement of Dissolved Oxygen in the Winery: A New Quality Assurance Criteria?", Internet Journal of Viticulture and Oenology, 14: 1-5 (2001).
Nikolantonaki, M., et al., "Measuring protection of aromatic wine thiols from oxidation by competitive reactions vs wine preservatives with ortho-quinones", Food Chemistry, 163: 61-67 (2014).
Nikolantonaki, M., et al., "Reactivity of volatile thiols with polyphenols in a wine-model medium: Impact of oxygen, iron, and sulfur dioxide", Analytica Chimica Acta, 660: 102-109 (2010).
Pozo-Bayón, M.A., et al., "Scientific evidences beyond the application of inactive dry yeast preparations in winemaking", Food Research International, 42: 754-761 (2009).
Ramirez-Gaona, M., et al., "YMDB 2.0: a significantly expanded version of the yeast metabolome database", Nucleic Acids Research, 45: D440-D445 (2017).
Rodriguez-Bencomo, J.J., et al., "Impact of Glutathione-Enriched Inactive Dry Yeast Preparations on the Stability of Terpenes during Model Wine Aging", Journal of Agr. And Food Chem., 62: 1373-1383 (2014).
Roullier-Gall, C., et al., "High precision mass measurements for wine metabolomics", frontiers in Chemistry, 2(102): 1-9 (2014).
Roullier-Gall, C., et al., "Integrating analytical resolutions in non-targeted wine metabolomics", Tetrahedron, 71: 2983-2990 (2015).
Roullier-Gall, C., et al., "Sulfites and the wine metabolome", Food Chemistry, 237: 106-113 (2017).
Shapiro, S.K., et al., "Conversion of 5'-Methylthiooadenosine into S-Adenosylmethionine by Yeast Cells", Biochimica et Biophysica Acta, 633: 176-180 (1980).
Stoscheck, C.M., "Quantitation of Protein", General methods for Handling Proteins and Enzymes, 6: 50-68 (1990).
Suhre, K., et al., "MassTRX: mass translator into pathways", Nucleic Acids Research, 36: W481-W484 (2008).
Suklje et al., "Inactive dry yeast application on grapes modify Sauvignon Blanc wine aroma", Food chemistry, vol. 197, Nov. 26, 2015, pp. 1073-1084.
Sumner, L.W., et al., "Proposed quantitative and alphanumeric metabolite identification metrics", Metabolomics, 10: 1047-1049 (2014).
Thomas, D., et al., "Metabolism of Sulfur Amino Acids in *Saccharomyces cerevisiae*", Microbiol. And Mol. Biol. Reviews, 505-532 (1997).
Tucci, A.F., et al., "Homocitrate Synthase from Yeast", Archives of Biochem. And Biophysics, 153: 742-750 (1972).
Tziotis, D., et al., "Kendrick-Analogous Network Visualisation of Ion Cyclotron Resonance Fourier Transform Mass Spectra: Improved Options for the Assignment of Elemental Compositions and the Classification of Organic Molecular Complexity", Eur. J. Mass Spectrom., 17: 415-421 (2011).
Gallone, Brigida et al., "Domestication and Divergence of *Saccharomyces cerevisiae* Beer Yeasts"; Cell 166, Sep. 8, 2016, pp. 1397-1410.
Sicard, Delphine et al., "Bread, Beer and Wine: Yeast Domestication in the *Saccharomyces sensustricto* Complex"; C. R. Biologies 334 (2011), pp. 229-236.
Randez-Gil, Francisca et al., "Genetic and Phenotypic Characteristics of Baker's Yeast: Relevance to Baking"; Annual Review of Food Science and Technology, 2013, 4:191-214.
Order Form for the Chinese Center of Industrial Culture Collection for Brewer's yeast—*Saccharomyces cerevisiae* CICC® 1532, Strain No. CICC1532; 2 pages.

* cited by examiner

FIGURES 7A, 7B, 7C, and 7D
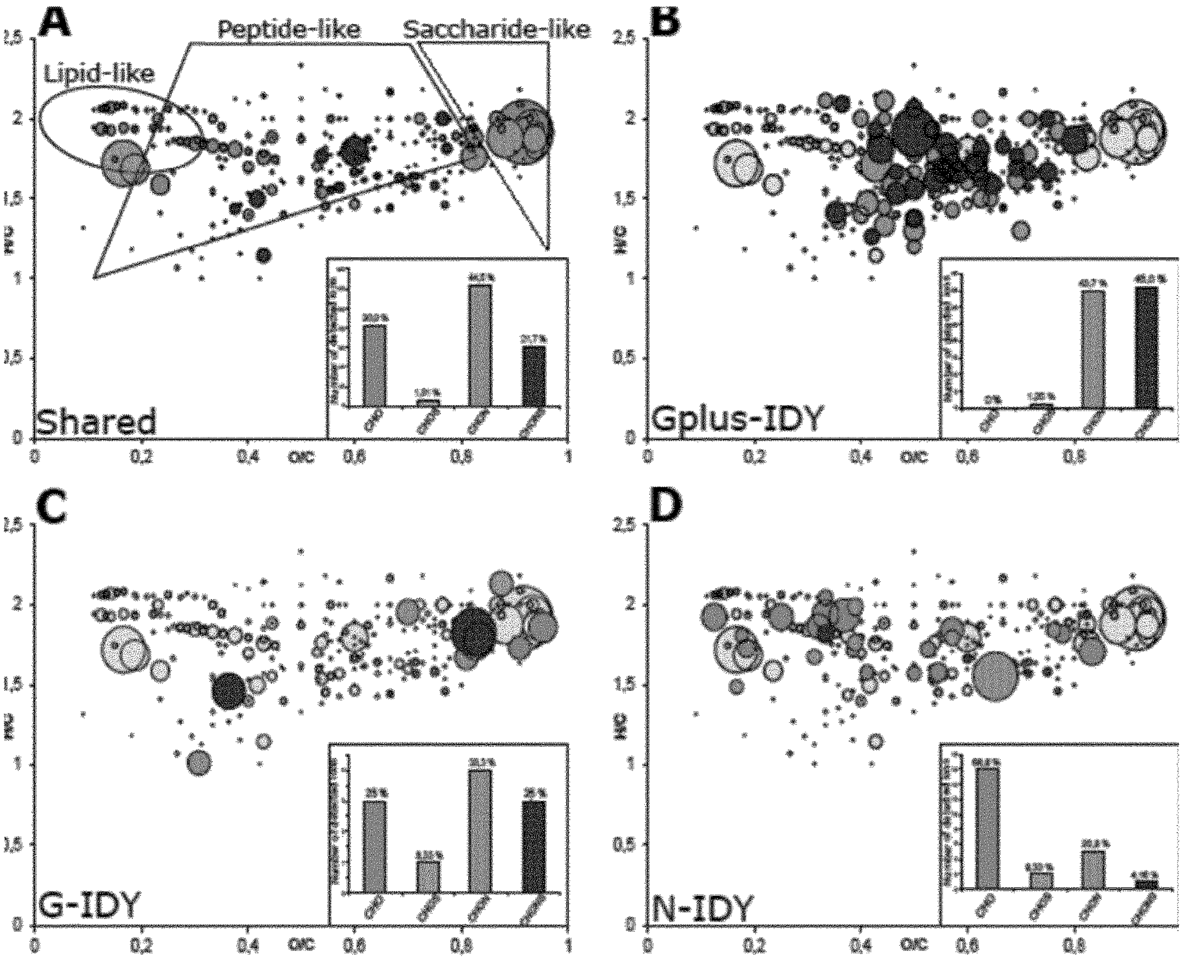

GLUTATHIONE-RICH YEAST AND ITS USE FOR PRESERVING WINES

FIELD

The present disclosure relates to a glutathione-rich yeast, its derivatives thereof and uses for preserving wines.

BACKGROUND OF THE INVENTION

The problems associated with the ageing of white wines are well known to wine growers. They manifest themselves through a loss of varietal aromas, a modified organoleptic profile and a brown coloration of the wines. Oxidation phenomena are to be related to these aromatic and chromatic changes. In particular, the browning of white wines is attributed to oxidative polymerizations of certain polyphenols. The latter, by reacting with oxygen, produce quinones and semiquinones. These compounds form brown pigments. The aromatic properties of the volatile thiols, once the latter have become complexed with the quinones, can no longer be expressed. Now, white wines are developed with the objective of obtaining fresh, fruity wines to be consumed quite rapidly, or else wines referred to as "premium" which are aged for several years. In both cases, it is necessary to protect the wines against oxidation and browning which can cause the organoleptic profile of these white wines to deteriorate. Specifically, deterioration of aromas and browning represent a loss of profits which is considerable in economic terms.

Some of the most potent varietal aroma compounds are volatile or varietal thiols like 3-mercaptohexan-1-ol (3MH), 3-mercaptohexyl acetate (3MHA) and 4-mercapto-4-methylpentan-2-one (4MM). Their presence is considered essential for creating unique varietal flavour attributes which contribute positively to wine. These volatile thiols are synthesized and released by the yeast from a range of precursors during alcoholic fermentation. Previous studies have shown that nitrogen deficiency reduces the aromatic quality of, for example, Sauvignon Blanc, as well as its potential for ageing. This is thought to be linked to the reduced synthesis of volatile thiol precursors, as well as of glutathione, which plays an important role in protecting volatile thiols from oxidation.

Glutathione is important in wine because it has the ability to scavenge ortho-quinones, main protagonists of color browning and aroma loss due to oxidation mechanisms. Because it has a very low oxydoreduction potential, it can act as a strong buffer in many cellular oxydoreduction reactions. It has been known for years that it is a more potent anti-oxidant than ascorbic acid. It then plays a critical role in preventing the oxidation of must phenols as it can react via its —SH group with caftaric acid—one of the most susceptible phenols to oxidation in musts and generate Grape Reaction Product (GRP) which is a stable and colorless compound (Moutounet et al, 2001). Notably, this mechanism has been shown for GSH and not for the other compounds present in must or in yeast, and possessing SH-group (such as cystein or glutamyl-cystein for instance). GSH can also compete with several thiols (aromatic compounds such as 3-mercapto-hexanol (3MH), its acetate 3-mercapto-hexanol acetate (3MH-A) and 4-methyl-mercapto-pentanone (4MMP)) present in wines under the form of precursors or aromatic molecules, for o-quinones thus protecting certain wine aromas (Dubourdieu et al, 2004). The effect of GSH on wine as a natural anti-oxidant for the preservation of wine aroma and colour is well understood now. Having high levels of glutathione in wine is then important for the preservation of aroma and color. The level of glutathione can vary in must as it is based on grape varietals, viticultural practices and the winemaking practices. In U.S. Pat. No. 8,268,372, a glutathione-rich yeast is introduced into a must in order to obtain fresh, fruitier white wines, with complex aromas, and that, during the ageing of these wines, the freshness of these aromas is preserved and browning is avoided.

While the effect of a glutathione-rich yeast for the prevention of defective ageing of white wines has been studied and reported, there remains a need for an improved glutathione-rich yeast with increased levels of glutathione with the ongoing need of preventing problems of defective aging through the introduction of yeast-rich with increased level of glutathione in the must or in the wine during the winemaking process before bottling.

SUMMARY

One aim of the present disclosure is the provision of a glutathione-rich yeast for preserving wines.

Another aim of the present disclosure is to provide a method of prevention of defective ageing white wines.

In accordance with the present disclosure, there is provided a glutathione-rich *Saccharomyces cerevisiae* strain deposited at Institut Pasteur (Collection rationale de cultures de micro-organismes (CNCM), Institut Pasteur, 25-28, Rue du Dr. Roux, 75724, Paris Cédex 15, France), on 20 Feb. 2019 under accession number CNCM I-5404. In an embodiment, the glutathione-rich *Saccharomyces cerevisiae* strain contains more than 0.5% of glutathione by weight relative to the weight of solids of the yeast. In another embodiment, the glutathione-rich *Saccharomyces cerevisiae* strain contains at least 1% of glutathione by weight relative to the weight of solids of the yeast. In a further embodiment, the glutathione-rich *Saccharomyces cerevisiae* strain is in one or more of the following forms: active dry yeast, inactivated dry yeast.

Still in accordance with the present disclosure, there is provided a glutathione-rich inactivated dry yeast comprising a first dipeptide having the formula $C_{12}H_{25}N_3O_3$ with a molecular weight of 259.3458 g/mole; and a second dipeptide having the formula $C_{12}H_{25}N_5O_3$ with a molecular weight of 287.3593 g/mole. In an embodiment, the first and second peptides are lysine-leucine and arginine-leucine dipeptides respectively. In an embodiment, the lysine-leucine and arginine-leucine dipeptides are in an amount ranging from 0.0001-20 wt. %, based on a total weight of the glutathione-rich inactivated yeast. In another embodiment, the glutathione-rich inactivated yeast is from a glutathione-rich *Saccharomyces cerevisiae* strain deposited at Institut Pasteur, on 20 Feb. 2019 under accession number CNCM I-5404. In yet another embodiment, the glutathione-rich inactivated yeast contains more than 2% of glutathione by weight relative to the weight of solids of the inactivated yeast. In a further embodiment, the glutathione-rich inactivated *Saccharomyces cerevisiae* strain contains at least 2% of glutathione by weight relative to the weight of solids of the inactivated yeast.

Still yet in accordance with the present disclosure, there is provided a method for the prevention of defective ageing white wines. During the preparation of the wine, yeast previously rich in glutathione is introduced into the must at the beginning of, during or after the alcoholic fermentation step, the yeast is a *Saccharomyces cerevisiae* strain deposited at Institut Pasteur, on 20 Feb. 2019 under accession number CNCM I-5404.

DESCRIPTION OF THE FIGURES

FIGS. 7A, 7B, 7C and 7D illustrate annotated masses common and unique to each IDY, colored and plotted according to their chemical compositions.

DETAILED DESCRIPTION OF THE INVENTION

Figure 1A:
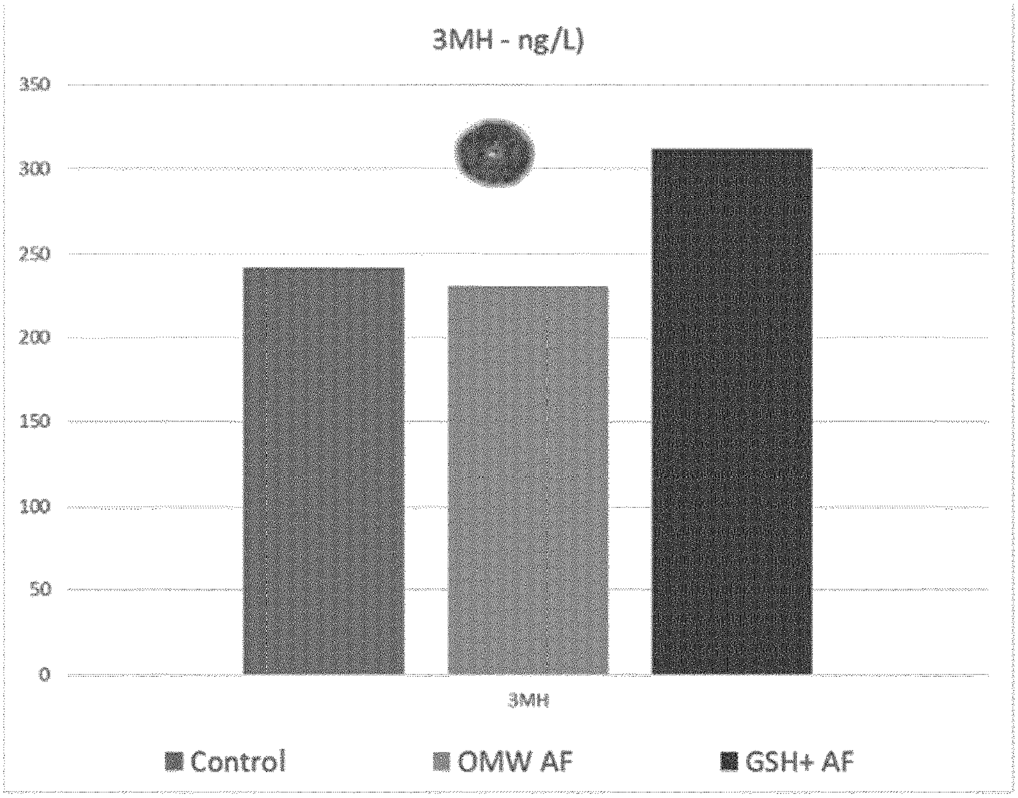
FIGS. 1A and 1B illustrate the impact of the rich-glutathione inactivated yeast of the present description on the varietal thiols content of finished wines when added into the must (Sauvignon Blanc South Africa 2018) at the beginning of the fermentation in comparison to the commercial product Optimum White™ (OMW).

It is widely assumed now that glutathione can play a protective role during alcoholic fermentation and during post-fermentation phases. The glutathione released by the yeast cell may react during aging or after bottling, with quinones to form a colorless complex (Grape Reaction Product) thereby preventing the same quinones to polymerize and form a brown complex, or to bind varietal thiols thus decreasing the aromatic expression.

The glutathione-rich yeast and its derivatives described in the present disclosure has many advantages. With the glutathione-rich yeast and its derivatives of the present description, it is possible to obtain, using only natural ingredients, quality white wines, meet the following criteria:—rounded wine—fresh and fruity—term stability of aromas—stability in the color of time. No addition of foreign substances such as chemical antioxidants is required, no complex manipulation is required. Surprisingly, it was found that the glutathione-rich yeast and its active or inactivated forms described in the present disclosure exhibited superior anti-radical scavenging properties than commercial product such as for example Optimum White™ (OMW) and yeast not rich in glutathione. This surprising feature provides to the glutathione-rich yeast and its active or inactivated forms described in the present disclosure superior anti-oxidant properties allowing them to better prevent problems of defective aging in wine.

More specifically, the present disclosure relates to a glutathione-rich *Saccharomyces cerevisiae* strain deposited at Institut Pasteur, on 20 Feb. 2019 under accession number CNCM I-5404.

The term "glutathione-rich yeast", as used herein, refers to yeast which have accumulated glutathione through biosynthesis as opposed to exogenous addition of glutathione to yeast. The biosynthesis process of accumulating glutathione in yeast is well known to those skilled in the art who know how to prepare it by means of one of the techniques at their disposal; see, for example, Catalino et al., 1992, Applied Microbiology and Biotechnology, Ed Springer-Verlag, pp. 141-146.

The term "glutathione-rich *Saccharomyces cerevisiae* strain" refers to a *Saccharomyces cerevisiae* strain which have accumulated glutathione through the same biosynthesis described above.

The term "glutathione-rich inactivated dry yeast" or "glutathione-rich yeast in inactivated dry yeast form" as used herein, refers to a glutathione-rich yeast described above that have been killed, by any physical, chemical or physico-chemical process known to those skilled in the art who know how to prepare it by means of one of the techniques at their disposal.

Likewise, the term "glutathione-rich inactivated *Saccharomyces cerevisiae* strain" or "glutathione-rich *Saccharomyces cerevisiae* strain in inactivated dry yeast from" as used herein, refers to a glutathione-rich *Saccharomyces cerevisiae* strain described above that have been killed with the same methods described above.

The term "glutathione" is intended to mean the molecule composed of the three amino acids glutamate-cysteine-glycine, in its oxidized or reduced form. Yeast in accordance with the present disclosure is a natural (e.g., not genetically modified using recombinant DNA/RNA technology) yeast strain mutant which has been obtained using classical mutagenesis/selection techniques available to the skilled person in the art. The ancestral yeast strain and the mutant yeast strain are non-genetically modified organisms, e.g., their genomic content has not been altered by the introduction of exogenous nucleic acid molecules or the removal of endogenous nucleic acid molecules using genetic engineering techniques.

The expression "N-IDY" in the context of the present disclosure means a non-glutathione-rich inactivated dry yeast. Still in the context of the present disclosure, the expression "G-IDY" or "Optimum White™ (OMW)" means a glutathione-rich inactivated yeasts commercially available (Lallemand) and made in accordance with the teachings of EP1706478B1. The rich yeast described in EP1706478B1 is an isolated natural yeast that was rich with glutathione in accordance with the techniques available to the skilled person in the art. The rich yeast described in EP1706478B1 has not been obtained using classical mutagenesis/selection techniques available to the skilled person in the art. Still yet in the context of the present disclosure, the expression "Gplus-IDY" means an improved glutathione-rich inactivated yeasts obtained in accordance with the teachings of the present disclosure. Yeast in accordance with the present disclosure is a natural (e.g., not genetically modified using recombinant DNA/RNA technology) yeast strain mutant which has been obtained using classical mutagenesis/selection techniques available to the skilled person in the art. The ancestral yeast strain and the mutant yeast strain are non-genetically modified organisms, e.g., their genomic content has not been altered by the introduction of exogenous nucleic acid molecules or the removal of endogenous nucleic acid molecules using genetic engineering techniques.

The glutathione-rich *Saccharomyces cerevisiae* strain contains more than 0.5% of glutathione by weight relative to the weight of solids of the yeast. Advantageously, the glutathione-rich yeast contains at least 1% of glutathione, at least 2% of glutathione, at least 3% of glutathione, at least 4% of glutathione, at least 5% of glutathione, at least 6% of glutathione, at least 7% of glutathione, at least 8% of glutathione, at least 9% of glutathione or at least 10% of glutathione by weight relative to the weight of solids of the yeast.

In an embodiment, the glutathione-rich *Saccharomyces cerevisiae* strain is in following forms: active dry yeast, inactivated dry yeast. When the glutathione-rich *Saccharomyces cerevisiae* strain is in inactivated dry yeast form, the inactivated dry yeast form comprises a first dipeptide having the formula C12H25N3O3 with a molecular weight of 259.3458 g/mole; and a second dipeptide having the formula C12H25N5O3 with a molecular weight of 287.3593 g/mole. In an embodiment, the first and second peptides are lysine-leucine and arginine-leucine dipeptides respectively. The lysine-leucine and arginine-leucine dipeptides are in an amount ranging from 0.0001-20 wt. %, based on a total weight of the glutathione-rich inactivated *Saccharomyces cerevisiae* strain; in an amount ranging from 0.0001-19.5 wt. %, based on a total weight of the glutathione-rich inactivated *Saccharomyces cerevisiae* strain, 0.0001-18.5 wt. %, based on a total weight of the glutathione-rich inactivated *Saccharomyces cerevisiae* strain; 0.0001-18 wt. %, based on a total weight of the glutathione-rich inactivated *Saccharomyces cerevisiae* strain; 0.0001-17.5 wt. %, based on a total weight of the glutathione-rich inactivated *Saccharomyces cerevisiae* strain; 0.0001-17 wt. %, based on a total weight of the glutathione-rich inactivated *Saccharomyces cerevisiae* strain; 0.0001-16.5 wt. %, based on a total weight of the glutathione-rich inactivated *Saccharomyces cerevisiae* strain; 0.0001-16 wt. %, based on a total weight of the glutathione-rich inactivated *Saccharomyces cerevisiae* strain; 0.0001-15.5 wt. %, based on a total weight of the glutathione-rich inactivated *Saccharomyces cerevisiae* strain; 0.0001-15 wt. %, based on a total weight of the glutathione-rich inactivated *Saccharomyces cerevisiae* strain; 0.0001-14.5 wt. %, based on a total weight of the glutathione-rich inactivated *Saccharomyces cerevisiae* strain; 0.0001-14 wt. %, based on a total weight of the glutathione-rich inactivated *Saccharomyces cerevisiae* strain; 0.0001-13.5 wt. %, based on a total weight of the glutathione-rich inactivated *Saccharomyces cerevisiae* strain; 0.0001-13 wt. %, based on a total weight of the glutathione-rich inactivated *Saccharomyces cerevisiae* strain; 0.0001-12.5 wt. %, based on a total weight of the glutathione-rich inactivated *Saccharomyces cerevisiae* strain; 0.0001-12 wt. %, based on a total weight of the glutathione-rich inactivated *Saccharomyces cerevisiae* strain; 0.0001-11.5 wt. %, based on a total weight of the glutathione-rich inactivated *Saccharomyces cerevisiae* strain; 0.0001-11 wt. %, based on a total weight of the glutathione-rich inactivated *Saccharomyces cerevisiae* strain; 0.0001-10.5 wt. %, based on a total weight of the glutathione-rich inactivated *Saccharomyces cerevisiae* strain; 0.0001-10 wt. %, based on a total weight of the glutathione-rich inactivated *Saccharomyces cerevisiae* strain; 0.0001-9.5 wt. %, based on a total weight of the glutathione-rich inactivated *Saccharomyces cerevisiae* strain; 0.0001-9 wt. %, based on a total weight of the glutathione-rich inactivated *Saccharomyces cerevisiae* strain; 0.0001-8.5 wt. %, based on a total weight of the glutathione-rich inactivated *Saccharomyces cerevisiae* strain; 0.0001-8 wt. %, based on a total weight of the glutathione-rich inactivated *Saccharomyces cerevisiae* strain; 0.0001-7.5 wt. %, based on a total weight of the glutathione-rich inactivated *Saccharomyces cerevisiae* strain; 0.0001-7 wt. %, based on a total weight of the glutathione-rich inactivated *Saccharomyces cerevisiae* strain; 0.0001-6.5 wt. %, based on a total weight of the glutathione-rich inactivated *Saccharomyces cerevisiae* strain; 0.0001-6 wt. %, based on a total weight of the glutathione-rich inactivated *Saccharomyces cerevisiae* strain; 0.0001-5.5 wt. %, based on a total weight of the glutathione-rich inactivated *Saccharomyces cerevisiae* strain; 0.0001-5 wt. %, based on a total weight of the glutathione-rich inactivated *Saccharomyces cerevisiae* strain; 0.0001-4.5 wt. %, based on a total weight of the glutathione-rich inactivated *Saccharomyces cerevisiae* strain; 0.0001-4 wt. %, based on a total weight of the glutathione-rich inactivated *Saccharomyces cerevisiae* strain; 0.0001-3.5 wt. %, based on a total weight of the glutathione-rich inactivated *Saccharomyces cerevisiae* strain 0.0001-3 wt. %, based on a total weight of the glutathione-rich inactivated *Saccharomyces cerevisiae* strain; 0.0001-2.5 wt. %, based on a total weight of the glutathione-rich inactivated *Saccharomyces cerevisiae* strain; 0.0001-2 wt. %, based on a total weight of the glutathione-rich inactivated *Saccharomyces cerevisiae* strain; 0.0001-1.5 wt. %, based on a total weight of the glutathione-rich inactivated *Saccharomyces cerevisiae* strain; 0.0001-1 wt. %, based on a total weight of the glutathi0.04one-rich inactivated *Saccharomyces cerevisiae* strain; 0.0001-0.5 wt. %, based on a total weight of the glutathione-rich inactivated *Saccharomyces cerevisiae* strain; 0.0001-0.4 wt. %, based on a total weight of the glutathione-rich inactivated *Saccharomyces cerevisiae* strain; 0.0001-0.3 wt. %, based on a total weight of the glutathione-rich inactivated *Saccharomyces cerevisiae* strain; 0.0001-0.2 wt. %, based on a total weight of the glutathione-rich inactivated *Saccharomyces cerevisiae* strain; 0.0001-0.1 wt. %, based on a total weight of the glutathione-rich inactivated *Saccharomyces cerevisiae* strain; 0.0001-0.05 wt. %, based on a total weight of the glutathione-rich inactivated *Saccharomyces cerevisiae* strain; 0.0001-0.04 wt. %, based on a total weight of the glutathione-rich inactivated *Saccharomyces cerevisiae* strain; 0.0001-0.03 wt. %, based on a total weight of the glutathione-rich inactivated *Saccharomyces cerevisiae* strain; 0.0001-0.02 wt. %, based on a total weight of the glutathione-rich inactivated *Saccharomyces cerevisiae* strain; 0.0001-0.01 wt. %, based on a total weight of the glutathione-rich inactivated *Saccharomyces cerevisiae* strain.

When the glutathione-rich *Saccharomyces cerevisiae* strain is in inactivated dry yeast form, the glutathione-rich inactivated *Saccharomyces cerevisiae* strain contains more than 2% of glutathione by weight relative to the weight of solids of the inactivated yeast. Advantageously, the glutathione-rich yeast contains at least 2% of glutathione, at least 3% of glutathione, at least 4% of glutathione, at least 5% of glutathione, at least 6% of glutathione, at least 7% of glutathione, at least 8% of glutathione, at least 9% of glutathione or at least 10% of glutathione by weight relative to the weight of solids of the inactivated yeast.

In an embodiment, the glutathione-rich *Saccharomyces cerevisiae* strain in inactivated dry yeast form contains at least 2% of glutathione, at least 2.1% of glutathione; at least 2.2% of glutathione; at least 2.3% of glutathione; at least 2.4% of glutathione; at least 2.4% of glutathione; at least 2.5% of glutathione; at least 2.6% of glutathione; at least 2.7% of glutathione; at least 2.8% of glutathione; at least 2.9% of glutathione; at least 3% of glutathione, at least 3.1% of glutathione; at least 3.2% of glutathione; at least 3.3% of glutathione; at least 3.4% of glutathione; at least 3.5% of glutathione; at least 3.6% of glutathione; at least 3.7% of glutathione; at least 3.8% of glutathione; at least 3.9% of glutathione; at least 4% of glutathione; at least 4.1% of glutathione; at least 4.2% of glutathione; at least 4.3% of glutathione; at least 4.4% of glutathione; at least 4.5% of glutathione; at least 4.6% of glutathione; at least 4.7% of glutathione; at least 4.8% of glutathione; or at least 4.9% of glutathione.

The present disclosure also relates to a glutathione-rich inactivated dry yeast comprising a first dipeptide having the formula C12H25N3O3 with a molecular weight of 259.3458 g/mole; and a second dipeptide having the formula C12H25N5O3 with a molecular weight of 287.3593 g/mole. In an embodiment, the first and second peptides are lysine-leucine and arginine-leucine dipeptides respectively. The yeast may be any suitable *Saccharomyces* or a non-*Saccharomyces* yeast as, for example, from the genera *Candida, Torula, Hanseniaspora, Hansenula, Kluyveromyces, Metschnikowia, Pichia, Starmerella, Torulaspora*. In an embodiment, the genera *Saccharomyces* includes, without limitation, *S. cerevisiae* or *S. cerevisiae* var. *boulardii.*

The word "comprising" in the claims may be replaced by "consisting essentially of" or with "consisting of," according to standard practice in patent law.

In an embodiment, the lysine-leucine and arginine-leucine dipeptides are in an amount ranging from 0.0001-20 wt. %, based on a total weight of the glutathione-rich inactivated yeast; in an amount ranging from 0.0001-19.5 wt. %, based on a total weight of the glutathione-rich inactivated *Saccharomyces cerevisiae* strain, 0.0001-18.5 wt. %, based on a total weight of the glutathione-rich inactivated *Saccharomyces cerevisiae* strain; 0.0001-18 wt. %, based on a total weight of the glutathione-rich inactivated *Saccharomyces cerevisiae* strain; 0.0001-17.5 wt. %, based on a total weight of the glutathione-rich inactivated *Saccharomyces cerevisiae* strain; 0.0001-17 wt. %, based on a total weight of the glutathione-rich inactivated *Saccharomyces cerevisiae* strain; 0.0001-16.5 wt. %, based on a total weight of the glutathione-rich inactivated *Saccharomyces cerevisiae* strain; 0.0001-16 wt. %, based on a total weight of the glutathione-rich inactivated *Saccharomyces cerevisiae* strain; 0.0001-15.5 wt. %, based on a total weight of the glutathione-rich inactivated *Saccharomyces cerevisiae* strain; 0.0001-15 wt. %, based on a total weight of the glutathione-rich inactivated *Saccharomyces cerevisiae* strain; 0.0001-14.5 wt. %, based on a total weight of the glutathione-rich inactivated *Saccharomyces cerevisiae* strain; 0.0001-14 wt. %, based on a total weight of the glutathione-rich inactivated *Saccharomyces cerevisiae* strain; 0.0001-13.5 wt. %, based on a total weight of the glutathione-rich inactivated *Saccharomyces cerevisiae* strain; 0.0001-13 wt. %, based on a total weight of the glutathione-rich inactivated *Saccharomyces cerevisiae* strain; 0.0001-12.5 wt. %, based on a total weight of the glutathione-rich inactivated *Saccharomyces cerevisiae* strain; 0.0001-12 wt. %, based on a total weight of the glutathione-rich inactivated *Saccharomyces cerevisiae* strain; 0.0001-11.5 wt. %, based on a total weight of the glutathione-rich inactivated *Saccharomyces cerevisiae* strain; 0.0001-11 wt. %, based on a total weight of the glutathione-rich inactivated *Saccharomyces cerevisiae* strain; 0.0001-10.5 wt. %, based on a total weight of the glutathione-rich inactivated *Saccharomyces cerevisiae* strain; 0.0001-10 wt. %, based on a total weight of the glutathione-rich inactivated *Saccharomyces cerevisiae* strain; 0.0001-9.5 wt. %, based on a total weight of the glutathione-rich inactivated *Saccharomyces cerevisiae* strain; 0.0001-9 wt. %, based on a total weight of the glutathione-rich inactivated *Saccharomyces cerevisiae* strain; 0.0001-8.5 wt. %, based on a total weight of the glutathione-rich inactivated *Saccharomyces cerevisiae* strain; 0.0001-8 wt. %, based on a total weight of the glutathione-rich inactivated *Saccharomyces cerevisiae* strain; 0.0001-7.5 wt. %, based on a total weight of the glutathione-rich inactivated *Saccharomyces cerevisiae* strain; 0.0001-7 wt. %, based on a total weight of the glutathione-rich inactivated *Saccharomyces cerevisiae* strain; 0.0001-6.5 wt. %, based on a total weight of the glutathione-rich inactivated *Saccharomyces cerevisiae* strain; 0.0001-6 wt. %, based on a total weight of the glutathione-rich inactivated *Saccharomyces cerevisiae* strain; 0.0001-5.5 wt. %, based on a total weight of the glutathione-rich inactivated *Saccharomyces cerevisiae* strain; 0.0001-5 wt. %, based on a total weight of the glutathione-rich inactivated *Saccharomyces cerevisiae* strain; 0.0001-4.5 wt. %, based on a total weight of the glutathione-rich inactivated *Saccharomyces cerevisiae* strain; 0.0001-4 wt. %, based on a total weight of the glutathione-rich inactivated *Saccharomyces cerevisiae* strain; 0.0001-3.5 wt. %, based on a total weight of the glutathione-rich inactivated *Saccharomyces cerevisiae* strain 0.0001-3 wt. %, based on a total weight of the glutathione-rich inactivated *Saccharomyces cerevisiae* strain; 0.0001-2.5 wt. %, based on a total weight of the glutathione-rich inactivated *Saccharomyces cerevisiae* strain; 0.0001-2 wt. %, based on a total weight of the glutathione-rich inactivated *Saccharomyces cerevisiae* strain; 0.0001-1.5 wt. %, based on a total weight of the glutathione-rich inactivated *Saccharomyces cerevisiae* strain; 0.0001-1 wt. %, based on a total weight of the glutathi0.04one-rich inactivated *Saccharomyces cerevisiae* strain; 0.0001-0.5 wt. %, based on a total weight of the glutathione-rich inactivated *Saccharomyces cerevisiae* strain; 0.0001-0.4 wt. %, based on a total weight of the glutathione-rich inactivated *Saccharomyces cerevisiae* strain; 0.0001-0.3 wt. %, based on a total weight of the glutathione-rich inactivated *Saccharomyces cerevisiae* strain; 0.0001-0.2 wt. %, based on a total weight of the glutathione-rich inactivated *Saccharomyces cerevisiae* strain; 0.0001-0.1 wt. %, based on a total weight of the glutathione-rich inactivated *Saccharomyces cerevisiae* strain; 0.0001-0.05 wt. %, based on a total weight of the glutathione-rich inactivated *Saccharomyces cerevisiae* strain; 0.0001-0.04 wt. %, based on a total weight of the glutathione-rich inactivated *Saccharomyces cerevisiae* strain; 0.0001-0.03 wt. %, based on a total weight of the glutathione-rich inactivated *Saccharomyces cerevisiae* strain; 0.0001-0.02 wt. %, based on a total weight of the glutathione-rich inactivated *Saccharomyces cerevisiae* strain; 0.0001-0.01 wt. %, based on a total weight of the glutathione-rich inactivated *Saccharomyces cerevisiae* strain.

The glutathione-rich inactivated yeast contains more than 2% of glutathione by weight relative to the weight of solids of the yeast. Advantageously, the glutathione-rich yeast contains at least 2% of glutathione, at least 3% of glutathione, at least 4% of glutathione, at least 5% of glutathione, at least 6% of glutathione, at least 7% of glutathione, at least 8% of glutathione, at least 9% of glutathione or at least 10% of glutathione by weight relative to the weight of solids of the yeast.

In an embodiment, the glutathione-rich inactivated yeast contains at least 2% of glutathione, at least 2.1% of glutathione; at least 2.2% of glutathione; at least 2.3% of glutathione; at least 2.4% of glutathione; at least 2.4% of glutathione; at least 2.5% of glutathione; at least 2.6% of glutathione; at least 2.7% of glutathione; at least 2.8% of glutathione; at least 2.9% of glutathione; at least 3% of glutathione, at least 3.1% of glutathione; at least 3.2% of glutathione; at least 3.3% of glutathione; at least 3.4% of glutathione; at least 3.5% of glutathione; at least 3.6% of glutathione; at least 3.7% of glutathione; at least 3.8% of glutathione; at least 3.9% of glutathione; at least 4% of glutathione; at least 4.1% of glutathione; at least 4.2% of glutathione; at least 4.3% of glutathione; at least 4.4% of glutathione; at least 4.5% of glutathione; at least 4.6% of glutathione; at least 4.7% of glutathione; at least 4.8% of glutathione; or at least 4.9% of glutathione.

In an embodiment, the glutathione-rich inactivated yeast is introduced in addition to the inoculated yeast to initiate fermentation. The glutathione is immediately released in must. If necessary, supplementation of glutathione-rich inactivated yeast in accordance with the present disclosure may be done immediately or later during the alcoholic fermentation.

In another embodiment, the glutathione-rich inactivated yeast can be used in winemaking to protect the wine against oxidation, therefore preserving the wine quality, color and aromas. In a further embodiment, the glutathione-rich inactivated yeast can be used for prevention of defective ageing white wines.

In a further embodiment, the glutathione-rich inactivated yeast is from a glutathione-rich *Saccharomyces cerevisiae* strain deposited at Institut Pasteur, on 20 Feb. 2019 under accession number CNCM I-5404.

The present disclosure further relates to a method for the prevention of defective ageing white wines, wherein, during the preparation of the wine, yeast previously rich in glutathione is introduced into the must at the beginning of, during or after the alcoholic fermentation step, the yeast is a *Saccharomyces cerevisiae* strain deposited at Institut Pasteur, on 20 Feb. 2019 under accession number CNCM I-5404.

In the method according to the present disclosure, said glutathione-rich yeast contains more than 0.5% of glutathione by weight relative to the weight of solids of the yeast. Advantageously, the glutathione-rich yeast contains at least 1% of glutathione, at least 2% of glutathione, at least 3% of glutathione, at least 4% of glutathione, at least 5% of glutathione, at least 6% of glutathione, at least 7% of glutathione, at least 8% of glutathione, at least 9% of glutathione or at least 10% of glutathione by weight relative to the weight of solids of the yeast.

The glutathione-rich yeast can be introduced in the must/wine at any time prior to bottling wine at the beginning of alcoholic fermentation, in the course of it, or even when the latter is finished, for example during barrel ageing if necessary. For reasons of mere convenience, it is recommended to introduce the beginning of fermentation.

For wine, we mean a fruit juice, a fermenting juice or in which the alcoholic fermentation is over, until a finished wine, possibly after barrel aging. When the wine is finished, it is filtered for bottling. At this point, for obvious practical reasons, it is difficult to envisage an intake of glutathione-rich yeasts.

In an embodiment, the glutathione-rich yeast in accordance with the present disclosure may also be used for carrying out the alcoholic fermentation. The glutathione is released immediately in the must during the fermentation or in wine.

According to an advantageous embodiment of the method according to the present disclosure, the glutathione-rich yeast is added into the must in an amount of 10 g to 100 g of solids per hectoliter (hL) of must, preferably 20 g/hL to 50 g/hL, and more preferably 20 g/hL to 40 g/hL.

The dosage of the amount of glutathione-rich yeast introduced into the must/wine can be adjusted according to various parameters such as the level of enrichment of glutathione yeast or the amplitude of the desired effect. Finally, the skilled person can determine the amount of yeast to be introduced, depending on the amount it wishes to make glutathione. Thus, according to an advantageous characteristic of the method according to the invention, the introduction into the wort glutathione-rich yeast produces a provision of at least 0.5 mg of glutathione per liter of must, at least 1 mg of glutathione per liter of must or at least 2 mg of glutathione per liter of must, the boundary top up to 100 mg/l although the contribution of the corresponding amounts of yeast are economically unacceptable.

In a previously reported embodiment, the glutathione-rich yeast can be introduced in the must/wine at any time prior to bottling wine at the beginning of alcoholic fermentation in the course of it, or prior to the start of the fermentation (during settling, after pressing) or during a pre-fermentative stabulation step, or even when fermentation is finished. In some cases, it is nevertheless advisable to wait a few hours after inoculation fermenting yeast.

In an embodiment, the glutathione-rich yeast can be introduced into the must/wine in the form of inactivated dry yeast but also in the form of active dry yeast.

When the glutathione-rich yeast is in inactivated dry yeast form, the inactivated dry form contains more than 2% of glutathione by weight relative to the weight of solids of the inactivated yeast. Advantageously, the glutathione-rich yeast contains at least 2% of glutathione, at least 3% of glutathione, at least 4% of glutathione, at least 5% of glutathione, at least 6% of glutathione, at least 7% of glutathione, at least 8% of glutathione, at least 9% of glutathione or at least 10% of glutathione by weight relative to the weight of solids of the inactivated yeast.

In an embodiment, the glutathione-rich yeast in inactivated dry form contains at least 2% of glutathione, at least 2.1% of glutathione; at least 2.2% of glutathione; at least 2.3% of glutathione; at least 2.4% of glutathione; at least 2.4% of glutathione; at least 2.5% of glutathione; at least 2.6% of glutathione; at least 2.7% of glutathione; at least 2.8% of glutathione; at least 2.9% of glutathione; at least 3% of glutathione, at least 3.1% of glutathione; at least 3.2% of glutathione; at least 3.3% of glutathione; at least 3.4% of glutathione; at least 3.5% of glutathione; at least 3.6% of glutathione; at least 3.7% of glutathione; at least 3.8% of glutathione; at least 3.9% of glutathione; at least 4% of glutathione; at least 4.1% of glutathione; at least 4.2% of glutathione; at least 4.3% of glutathione; at least 4.4% of glutathione; at least 4.5% of glutathione; at least 4.6% of glutathione; at least 4.7% of glutathione; at least 4.8% of glutathione; or at least 4.9% of glutathione.

According to one embodiment of the method according to the present disclosure, the glutathione-rich yeast in inactivated dry form is likewise added into the must in an amount of 10 g to 100 g of solids per hectoliter (hl) of must, preferably 20 g/hL to 50 g/hL, and more preferably 20 g/hL to 40 g/hL.

In one embodiment of the method according to the present disclosure, the introduction into the must/wine of glutathione-rich yeast in inactivated form produces a provision of at least 2 mg of glutathione per liter of must, at least 4 mg of glutathione per liter of must, at least 8 mg of glutathione per liter of must, or at least 10 mg of glutathione per liter of must, the boundary top up to 100 mg/l although the contribution of the corresponding amounts of yeast are economically unacceptable.

When the glutathione-rich yeast is in inactivated dry yeast form, the inactivated dry form comprises a first dipeptide having the formula C12H25N3O3 with a molecular weight of 259.3458 g/mole; and a second dipeptide having the formula C12H25N5O3 with a molecular weight of 287.3593 g/mole. In an embodiment, the first and second peptides are lysine-leucine and arginine-leucine dipeptides respectively. The lysine-leucine and arginine-leucine dipeptides are in an amount ranging from 0.0001-20 wt. %, based on a total weight of the glutathione-rich inactivated *Saccharomyces cerevisiae* strain; in an amount ranging from 0.0001-19.5 wt. %, based on a total weight of the glutathione-rich inactivated *Saccharomyces cerevisiae* strain, 0.0001-18.5 wt. %, based on a total weight of the glutathione-rich inactivated *Saccharomyces cerevisiae* strain; 0.0001-18 wt. %, based on a total weight of the glutathione-rich inactivated *Saccharomyces cerevisiae* strain; 0.0001-17.5 wt. %, based on a total weight of the glutathione-rich inactivated *Saccharomyces cerevisiae* strain; 0.0001-17 wt. %, based on a total weight of the glutathione-rich inactivated *Saccharomyces cerevisiae* strain; 0.0001-16.5 wt. %, based on a total weight of the glutathione-rich inactivated *Saccharomyces cerevisiae* strain; 0.0001-16 wt. %, based on a total weight of the glutathione-rich inactivated *Saccharomyces cerevisiae* strain; 0.0001-15.5 wt. %, based on a total weight of the glutathione-rich inactivated *Saccharomyces cerevisiae* strain; 0.0001-15 wt. %, based on a total weight of the glutathione-rich inactivated *Saccharomyces cerevisiae* strain; 0.0001-14.5 wt. %, based on a total weight of the glutathione-rich inactivated *Saccharomyces cerevisiae* strain; 0.0001-14 wt. %, based on a total weight of the glutathione-rich inactivated *Saccharomyces cerevisiae* strain; 0.0001-13.5 wt. %, based on a total weight of the glutathione-rich inactivated *Saccharomyces cerevisiae* strain; 0.0001-13 wt. %, based on a total weight of the glutathione-rich inactivated *Saccharomyces cerevisiae* strain; 0.0001-12.5 wt. %, based on a total weight of the glutathione-rich inactivated *Saccharomyces cerevisiae* strain; 0.0001-12 wt. %, based on a total weight of the glutathione-rich inactivated *Saccharomyces cerevisiae* strain; 0.0001-11.5 wt. %, based on a total weight of the glutathione-rich inactivated *Saccharomyces cerevisiae* strain; 0.0001-11 wt. %, based on a total weight of the glutathione-rich inactivated *Saccharomyces cerevisiae* strain; 0.0001-10.5 wt. %, based on a total weight of the glutathione-rich inactivated *Saccharomyces cerevisiae* strain; 0.0001-10 wt. %, based on a total weight of the glutathione-rich inactivated *Saccharomyces cerevisiae* strain; 0.0001-9.5 wt. %, based on a total weight of the glutathione-rich inactivated *Saccharomyces cerevisiae* strain; 0.0001-9 wt. %, based on a total weight of the glutathione-rich inactivated *Saccharomyces cerevisiae* strain; 0.0001-8.5 wt. %, based on a total weight of the glutathione-rich inactivated *Saccharomyces cerevisiae* strain; 0.0001-8 wt. %, based on a total weight of the glutathione-rich inactivated *Saccharomyces cerevisiae* strain; 0.0001-7.5 wt. %, based on a total weight of the glutathione-rich inactivated *Saccharomyces cerevisiae* strain; 0.0001-7 wt. %, based on a total weight of the glutathione-rich inactivated *Saccharomyces cerevisiae* strain; 0.0001-6.5 wt. %, based on a total weight of the glutathione-rich inactivated *Saccharomyces cerevisiae* strain; 0.0001-6 wt. %, based on a total weight of the glutathione-rich inactivated *Saccharomyces cerevisiae* strain; 0.0001-5.5 wt. %, based on a total weight of the glutathione-rich inactivated *Saccharomyces cerevisiae* strain; 0.0001-5 wt. %, based on a total weight of the glutathione-rich inactivated *Saccharomyces cerevisiae* strain; 0.0001-4.5 wt. %, based on a total weight of the glutathione-rich inactivated *Saccharomyces cerevisiae* strain; 0.0001-4 wt. %, based on a total weight of the glutathione-rich inactivated *Saccharomyces cerevisiae* strain; 0.0001-3.5 wt. %, based on a total weight of the glutathione-rich inactivated *Saccharomyces cerevisiae* strain; 0.0001-3 wt. %, based on a total weight of the glutathione-rich inactivated *Saccharomyces cerevisiae* strain; 0.0001-2.5 wt. %, based on a total weight of the glutathione-rich inactivated *Saccharomyces cerevisiae* strain; 0.0001-2 wt. %, based on a total weight of the glutathione-rich inactivated *Saccharomyces cerevisiae* strain; 0.0001-1.5 wt. %, based on a total weight of the glutathione-rich inactivated *Saccharomyces cerevisiae* strain; 0.0001-1 wt. %, based on a total weight of the glutathione-rich inactivated *Saccharomyces cerevisiae* strain; 0.0001-0.5 wt. %, based on a total weight of the glutathione-rich inactivated *Saccharomyces cerevisiae* strain; 0.0001-0.4 wt. %, based on a total weight of the glutathione-rich inactivated *Saccharomyces cerevisiae* strain; 0.0001-0.3 wt. %, based on a total weight of the glutathione-rich inactivated *Saccharomyces cerevisiae* strain; 0.0001-0.2 wt. %, based on a total weight of the glutathione-rich inactivated *Saccharomyces cerevisiae* strain; 0.0001-0.1 wt. %, based on a total weight of the glutathione-rich inactivated *Saccharomyces cerevisiae* strain; 0.0001-0.05 wt. %, based on a total weight of the glutathione-rich inactivated *Saccharomyces cerevisiae* strain; 0.0001-0.04 wt. %, based on a total weight of the glutathione-rich inactivated *Saccharomyces cerevisiae* strain; 0.0001-0.03 wt. %, based on a total weight of the glutathione-rich inactivated *Saccharomyces cerevisiae* strain; 0.0001-0.02 wt. %, based on a total weight of the glutathione-rich inactivated *Saccharomyces cerevisiae* strain; 0.0001-0.01 wt. %, based on a total weight of the glutathione-rich inactivated *Saccharomyces cerevisiae* strain.

In an alternate embodiment, the glutathione-rich yeast can be introduced into the must and/or wine several times and in different forms of combination of inactivated dry yeast and/or active dry yeast. The glutathione-rich active yeast may be introduced, for example, at the same time that the must is inoculated with the fermentation yeasts, then adding a second quantity of glutathione-rich yeast during the fermentation, for example in an inactivated form.

Finally, in accordance with another embodiment, the glutathione-rich yeast can be introduced into the must in one or more of the following: live yeast, inactivated yeast, dried or liquid.

In an embodiment, the glutathione-rich yeast is introduced in addition to the inoculated yeast to initiate fermentation. In a further embodiment, the yeast used for the fermentation of the worth may be a glutathione-rich yeast in accordance with the present disclosure. The glutathione is released in wine, after the fermentation. A single seeding of the glutathione-rich yeast may be needed before fermentation. If necessary, supplementation of glutathione-rich yeast in accordance with the present disclosure may be done immediately or later during the fermentation or ageing.

Thus, in a particular embodiment of the method according to the present disclosure, the glutathione-rich yeast is at least partly consisting of the yeast inoculated into the must in order to carry out the alcoholic fermentation.

In accordance with a method for preparing a wine in accordance with the present disclosure, the must has specific characteristics which confer on the wine finally obtained the good preservation properties described above, attributable to the presence of the glutathione-rich yeast strain of the present disclosure. Another subject of the present disclosure is thus a must, such as a grape must, in which an alcoholic fermentation occurs (or has occurred), comprising the glutathione-rich yeasts of the present disclosure. These yeasts are, for example, *Saccharomyces cerevisiae* and non-*Saccharomyces* having an enological advantage.

It will be understood that the above described method is primarily intended for the preparation of white wines, these being particularly affected by the problems of defective aging. It will be especially applied to the prevention of browning of white wine after bottling.

EXAMPLES

Example 1—Quantitation of Thiols in Dried Yeast Samples

Rich yeast is characterized by assaying its thiols content according to the method below.

1. Reagents and Standards

Standards:

Glutathione (GSH), 99% (Sigma Aldrich)

γ-glutamylsysteine (γ-Glu-Cys), 88% (Sigma Aldrich)

Cystein (Cys), 99% (Fluka)

Reagents:

Formic acid, 98% (ULTRA)

EDTA disodium salt dehydrate (C10H14N2Na2O8*H2O), 99.0% (Biotechnology Grade) (Amresco)

Acid Chloridric HCl, 37% (ACS) (Riedel de Haen)

DTNB (5,5'-dithiobis-2-nitrobenzoicacid) (Sigma)

Sodium hydroxyde NaOH (ACS) (Riedel de Haen)

MilliQ water (Millipore)

2. Reagents Preparation

Solvent A1: Water+0.1% Formic Acid

Take 1000 ml graduated volumetric flask, add ~500 ml of milliQ water, then add 1 ml of formic acid (98%) and finally add milliQ water up to 1000 ml.

Solvent B1: Acetonitrile+0.1% Formic Acid

Take 1000 ml graduated volumetric flask, add ~500 ml of acetonitrile, then add 1 ml of formic acid (98%) and finally add acetonitrile up to 1000 ml.

Preparation of 0.1 N Formic Acid Solution:

Take 500 ml graduated volumetric flask, add ~250 ml of milliQ water, then add 1.925 ml 98% formic acid and dilute it with milliQ water up to 500 ml.

(0.1 mol/L*46.03 g/mol)/1.22 g/ml/0.98=3.85 ml/L

Preparation TE8 Solution:

Weigh 6.05 g Tris(hydroxymethyl)aminomethane and 1,1167 g EDTA disodium salt dehydrate in a 1000 ml volumetric graduated flask and add 900 ml of milliQ water to dissolve them, then adjust pH to 8 using 1N HCl (~38 ml), add water up to 1000 ml.

Preparation 1N HCl Solution:

36.46 g/mol/1.22 g/ml/0.37=80.7709 ml 37% HCl/1 L $H_2O$ 8.0771 ml 37% HCl diluted with water up to 100 ml.

Preparation 0.1 N NaOH Solution:

0.1 mol/L*39.9971 g/mol=3.9997 g NaOH/1 L $H_2O$ 1 g NaOH diluted with water up to 250 ml.

3. Procedures 3.1. Standards Preparation

Stock-Standard Solution (Std-Stock) Preparation:

Dissolve GSH (~12-13 mg), g-glu-cys (~11-2 mg) and Cys (~8-9 mg) in 5 ml of 0.1 N formic acid solution.

Divide the stock into aliquots in 1.5 ml Eppendorf™ tubes and keep the stock-standard solution at −20° C.

Working Standard Solution (Std):

Prepare 6 different dilutions in 0.1 N of formic acid from standard stock: 1×; 5×; 10×; 20×; 30×; 40×

3.2. DTNB (5,5'-dithiobis-2-nitrobenzoicacid) Solutions Preparation 0.01 mM DTNB Stock-Solution Preparation:

39.6 mg DTNB+8 ml TE8+2 ml 0.1 N NaOH.

DTNB (0.0008 mM) Working Solution:

8 ml DTNB stock-solution+92 ml TE8 solution.

Standard Solution Derivatization:

0.1 ml std+4.9 ml DTNB work-solution (50× dilution), reaction time was about 10 mM at room temperature 4. Sample Preparation 1. Transfer an accurately weighted sample (~0.2 g dwt) into 15 ml centrifuge tube.
2. Add 5 ml 0.1 N formic acid; keep at room temperature for 1 h, with frequent vortex shaking.
3. Centrifuge at 11 500 rpm for 10 min at 10° C.
4. Add 0.1 ml of supernatant to 4.9 ml of DNTB working solution, vortex.
5. Keep prepared solution 10 min at room temperature.
6. Add derivated sample into UPLC vial.

5. Analysis of the Derivated Sample by Ultra-Performance Liquid Chromatography (UPLC™)

6. Calculation of the Thiols Content in the Yeast:

The thiols content in the yeast is calculated in accordance with the following equation:

$$Cy=(\mathrm{CUPLC}*V1*V3)/(1000*m*S)$$

Cy—thiol concentration in dried yeast sample (mg/g),

CUPLC—thiol concentration from UPLC (mg/L),

V1—volume of added extraction solution (0.1 N formic acid) (ml),

V3—dilution factor m—sample weight (g)

S—solid content of the sample, %

1000—conversion factor to convert L to ml.

7. Calculation of the Total Thiols (Based on GSH Eqv) in the Sample $$GSH(\text{eqv})=CGSH+(C\ \gamma\text{-glycys}/M\ \gamma\text{-glycys}+Ccys/Mcys)*MGSH$$

C—respective determined concentration of either γ-glutamylsysteine or cysteine

M—respective molecular weight of either γ-glutamylsysteine, cysteine or GSH

Example 2

This example illustrate the impact of the inactivated yeast in accordance with the present invention (GPlus-IDY) in trials on a Sauvignon Blanc must (South Africa 2018) against the Optimum White™, a glutathione rich inactivated yeasts commercially available (Lallemand) and obtained in accordance with the teachings of EP1706478B1.

South-African Sauvignon Blanc grapes harvested in 2018 were pressed. After pressing, a must was obtained and clarified then separated into three 50 L-tanks for the alcoholic fermentation. The three musts were all inoculated the same way with the yeast Lalvin QA23. After the innoculation of the yeast, Optimum White™ was added at a rate of 40 g/hL into the first fermentation tank ("OMW" treatment tank), and the inactivated yeast in accordance with the present invention (Gplus) was added at a rate of 40 g/hL to a second fermentation tank (the "GSH+" treatment tank). The last fermentation tank, the "Control" fermentation tank didn't get any inactivated yeast addition.

Figure 1B:
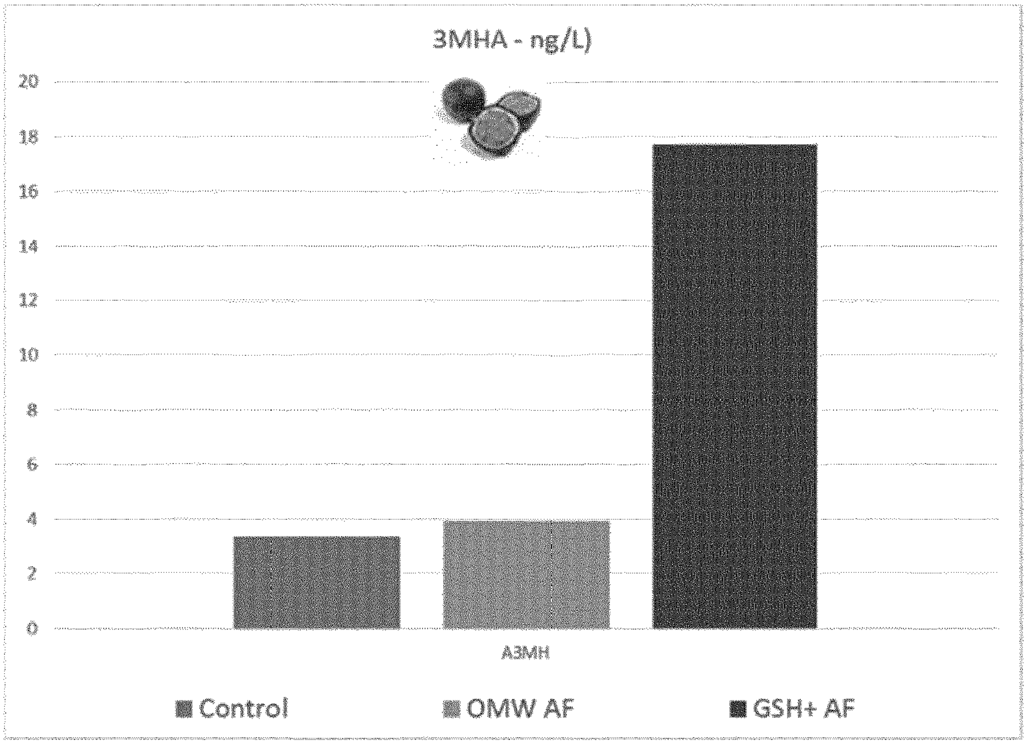

After the alcoholic fermentation, the wines obtained in each three fermentation thanks were stabilized according to methods well known to the skilled person in the art (SO2 addition) and then all bottled according to the same usual method, in standardized conditions. The volatile compounds were analyzed and significant differences were found, namely on the volatile thiols composition. FIGS. 1A and 1B shows higher amount of 3-mercapto-hexanol (3MH) and its acetate derivative (3MHA) in wines were the inactivated yeast of the present invention (GPlus inactivated yeast) was added into the must at the beginning of the fermentation. These volatile thiols are aromatic molecules with a strong impact on the aromatic profiles (exotic fruit, passion fruit notes) and are also good markers of oxidation. The higher the quantity of volatile thiols is the better the resistance of the wine to oxidation.

Example 3

This example illustrate the impact of the inactivated yeast in accordance with the present invention (GPlus-IDY) in trials on a Sauvignon Blanc must (Bordeaux 2017) against the Optimum White™ (OMW), a glutathione rich inactivated yeasts commercially available (Lallemand).

Bordeaux Sauvignon Blanc grapes harvested in 2017 were pressed. After pressing, a must was obtained and clarified, then separated into three 50 L-tanks for the alcoholic fermentation. The three musts were all inoculated the same way with the selected yeast Lalvin Cross Evolution. After inoculation with the yeast, Optimum White™ was added at a rate of 40 g/hL into the first fermentation tank ("OMW" treatment tank), and the inactivated yeast in accordance with the present invention (Gplus) was added at a rate of 40 g/hL to a second fermentation tank (the "GSH+" treatment tank). The last fermentation tank, the "Control" fermentation tank didn't get any inactivated yeast addition.

Figure 2A:
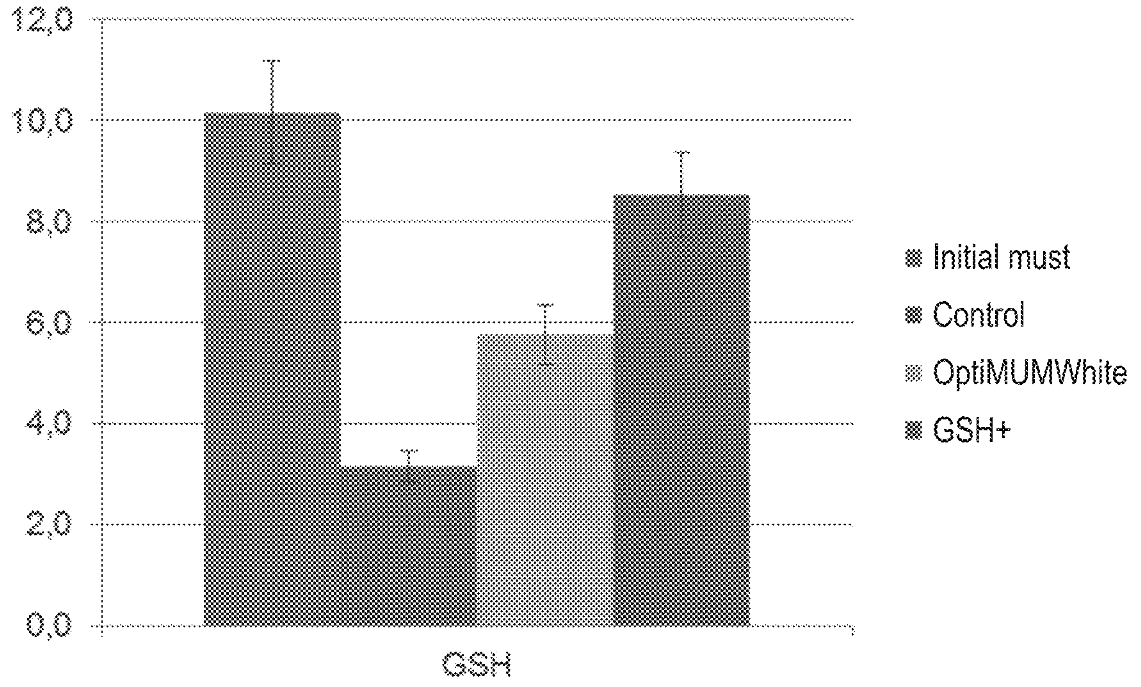
FIGS. 2A and B illustrate the impact of the rich-glutathione inactivated yeast of the present description on the varietal thiols content of finished wines when added into the must (Sauvignon Blanc Bordeaux 2017) at the beginning of the fermentation in comparison to the commercial product Optimum White™ (OMW).
Figure 2B:
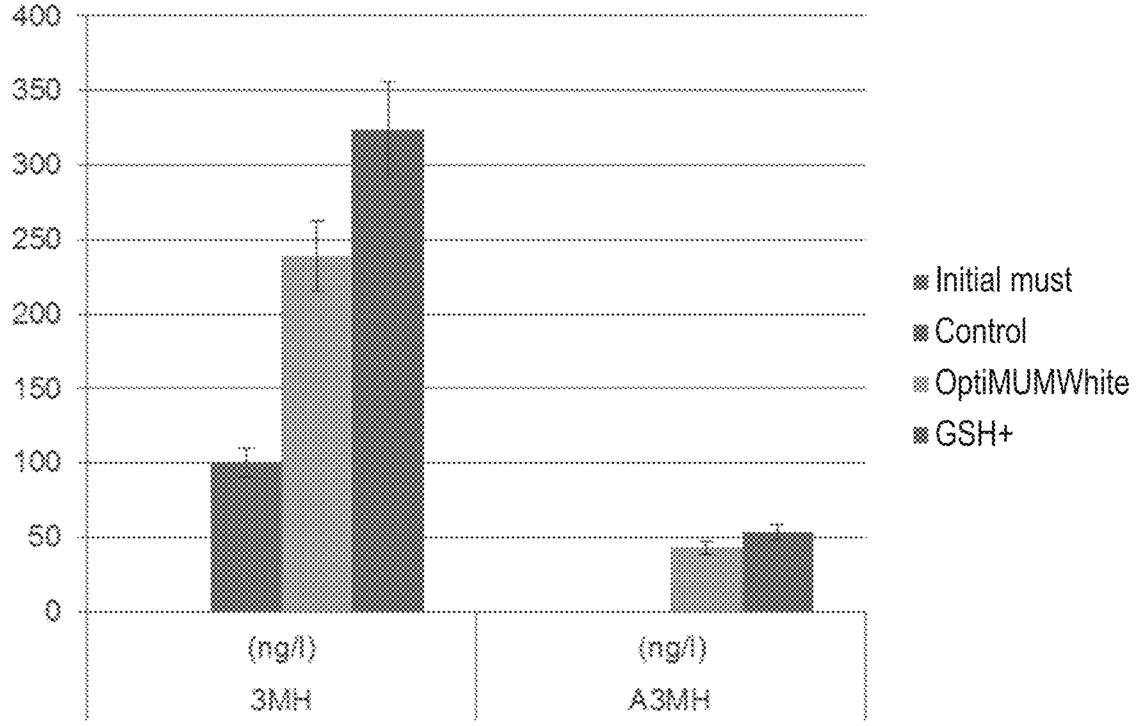

After the alcoholic fermentation, the wines obtained in each three fermentation thanks were stabilized according to methods well known to the skilled person in the art (SO2 addition) and then all bottled according to the same usual method, in standardized conditions. The volatile compounds were analyzed and significant differences were found, namely on the volatile thiols composition. FIGS. 2A and 2B shows higher amount of 3-mercapto-hexanol (3MH) and its acetate derivative (3MHA) in wines were the inactivated yeast of the present invention (GPlus inactivated yeast) was added into the must at the beginning of the fermentation. These volatile thiols are aromatic molecules with a strong impact on the aromatic profiles (exotic fruit, passion fruit notes) and are also good markers of oxidation. The higher the quantity of volatile thiols is the better the resistance of the wine to oxidation.

The GSH content of the resulting wines treated with GSH-rich inactivated yeasts at the beginning of their respective fermentation were higher than the control untreated. Surprisingly, wines treated with the inactivated yeast in accordance with the present invention (GPlus inactivated yeast) had a much higher GSH content than the wines treated with Optimum White™.

Example 4

During the 2018 harvest season, new trials have been set up with the objective of evaluating the impact on wines of the inactivated yeast in accordance with the present invention (GPlus inactivated yeast) in the context of an early addition to the must, for example, prior to yeast inoculation, during the clarification step and namely the pre-fermentative stabulation (macerations on the lees from pressing).

In each of these trials presented below, the comparison was made between a control without any addition, and addition of the inactivated yeast in accordance with the present invention (Gplus inactivated yeast "GSH+") in the context of an addition during the classical settling (around 12 hours" and of cold stabulation (6 days at 5° C.).

In the Val de Loire trial, additional comparative treatments were set up: The Optimum White™ was tested during the classical settling and also during the cold stabulation. Two other comparative treatments have also been setup, consisting in treating the must with inactivated yeast in accordance with the present invention (GPlus inactivated yeast) and Optimum White™ immediately after the inoculation of the must with the live yeast.

Example 4a: Trial LED in South West of France (Gers), Grapes of Sauvignon Blanc were Harvested in 2018

Figure 3:
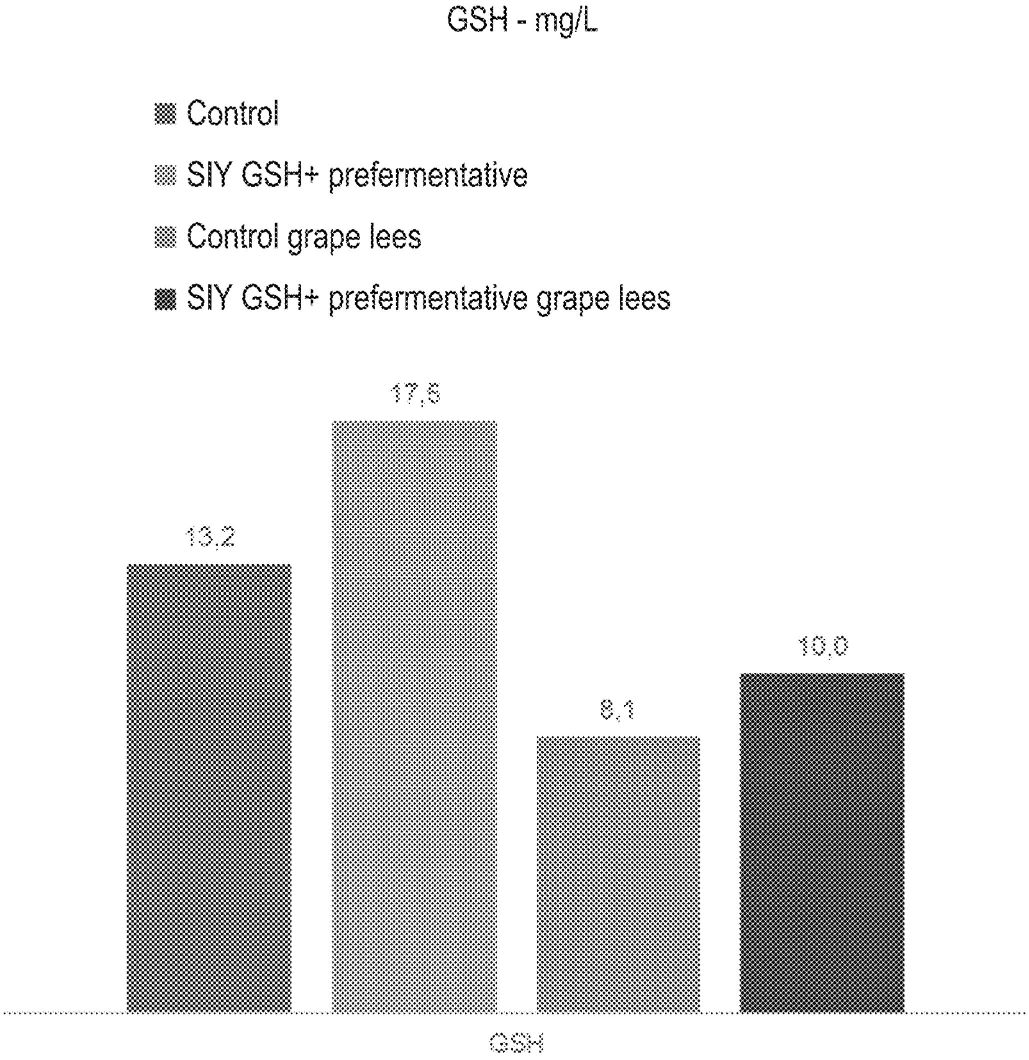
FIG. 3 illustrates the GSH concentrations, at settling or at the beginning of the pre-fermentative stabulation, in must (Sauvignon Blanc Gers, France 2018) treated with the inactivated yeast in accordance with the present invention (GPlus inactivated yeast) vs the untreated control.

As shown in FIG. 3, the GSH concentration is higher whatever the timing of addition in the must treated with the inactivated yeast in accordance with the present invention (GPlus inactivated yeast) vs the untreated control.

Example 4b: Trial LED in Val De Loire, with Grapes of Sauvignon Blanc Harvested in 2018

The FIGS. 4*a*, 4*b*, 4*c* and 4*d* below, illustrate the impact of the inactivated yeast in accordance with the present invention (GPlus inactivated yeast) on the three major volatile thiols levels (3MH, 3MHA and 4MMP) after bottling. The Optimum White™ (OMW) and the inactivated yeast in accordance with the present invention (Gplus) both have a positive impact on the major volatile thiols level. However, the inactivated yeast in accordance with the present invention (GPlus) is surprisingly more effective, especially in the context of an addition during the cold stabulation (6 days at 5° C.).

In the context of a classical use of such GSH-inactivated yeast, the inactivated yeast in accordance with the present invention (GPlus) was found to show a surprisingly greater impact than Optimum White™.

The impact of the products on GSH content after bottling is consistently showing the same trend as for volatile thiols.

Example 5

In this example, three different inactivated yeast products were compared. Soluble fractions in several solvents were studied to have a global overview of the compounds released by these enological products. Characterization was done by crossing targeted and untargeted analysis. Putative identification of both the most intense compounds and some specific compounds to each IDY was done.

Abbreviations Used

IDY, inactivated dry yeast; GSH, glutathione; MS, mass spectrometry; WSF, water soluble fraction; MWSF, model wine soluble fraction; MSF, methanol soluble fraction; GPC, gel permeation chromatography; HPLC, high pressure liquid chromatography; DAD, diode array detector; LMW, low molecular weight; LC-Q-ToF-MS, Liquid chromatography quadrupole time of flight mass spectrometry; RP-LC, reversed phase liquid chromatography; (−)FT-ICR-MS, Negative mode Fourier-transform ion cyclotron resonance mass spectrometry; S/N, Signal/Noise; kDa, kilo Dalton; Log P, partition coefficient

Material and Methods

Sample Preparation

Three inactivated dry yeasts (IDY) were obtained from Lallemand (Blagnac, France). These products were obtained at a laboratory scale process allowing optimizing chemical, physical and nutritional features of the bio-process in order to maximize the intracellular concentration of metabolites, notably glutathione. Two inactivated dry yeasts were specifically produced from different yeast strains to increase the bioavailability of glutathione (the inactivated yeast described in EP1706478B1 (G-IDY) and the inactivated yeast in accordance with the present invention (Gplus-IDY)). The third inactivated dry yeasts (N-IDY) was made with the same strain than G-IDY without following the specific process of GSH accumulation. The three IDY products were aliquoted in pre-weighed 2 mL vials under a low oxygen pressure and kept at −18° C. in dark.

Three different extractions were done to obtain: the acidified Water-Soluble Fraction (WSF) from ultrapure water (18.2 MΩ, Millipore, Germany) with 0.01% (v/v) formic acid at pH 3.2, the Model Wine Soluble Fraction (MWSF), from 12% (v/v) ethanol in ultrapure water with 0.01% (v/v) formic acid at pH 3.2, and the Methanol Soluble Fraction (MSF), from methanol with 0.1% (v/v) formic acid. IDYs were suspended at 4 g/L and soluble fractions were obtained after 1 h stirring at room temperature in dark. Samples were then centrifuged (12,000 g, 5 min, 4° C.) and the supernatants were aliquoted and stored under nitrogen at 4° C. until analysis. All samples were prepared in triplicate.

Gel Permeation Chromatography (GPC)

GPC was performed with a high-performance liquid chromatography (HPLC) (Elite LaChromElite, VWR, Radnor, Pennsylvanie) coupled to a DAD/Fluorescence detector (Coelho et al., 2017). 50 μL of sample were injected through a column Yarra 3μ SEC-2000 300×7.8 mm (Phenomenex, Sartrouville, France) connected to a guard column SecurityGuard (Phenomenex, Sartrouville, France). Elution was performed with hydro-alcoholic solution [12% (v/v) ethanol, 6 g/L of tartaric acid at pH 3.5] in an isocratic gradient (500 μL/min which correspond to a pressure of 75 bars)) for 45 min. The temperature of the sampler and the column were kept constant at 4° C. and 25° C. respectively during analysis. Fluorescence detector was set at 280 nm for the excitation wavelength and 350 nm for the emission wavelength, and the DAD enabled absorption spectra acquisition from 200 to 400 nm. Data were acquired with the EZChrom Elite (Agilent Technologies, Santa Clara, California) software, exported as .dat converted into .asc and handled with CHROMuLAN v0.79 (PiKRON Ltd.). Data were calibrated against low molecular weight standards mix (LMW Gel Filtration calibration kits, GE Healthcare, Buckinghamshire) with the following standards: Conalbumin (75 kDa), Ovalbumin (43 kDa), Ribonuclease A (13.7 kDa), Aprotinin (6.5 kDa) and Angiotensine (1.1 kDa). Elution times were converted into molecular weight masses according to a calibration curve (not shown).

Identification of Metabolites by LC-Q-ToF-MS/MS

The separation was done with an ultra-high-pressure liquid chromatography (Dionex Ultimate 3000, ThermoFischer) coupled to a MaXis plus MQ ESI-Q-TOF mass spectrometer (Bruker, Bremen, Germany). The non-polar and low polar metabolites were separated in reversed phase liquid chromatography (RP-LC) by injecting 5 μL in an Acquity UPLC BEH C18 1.7 μm column 100×2.1 mm (Waters, Guyancourt, France). Elution was performed at 40° C. by (A) acidified water (0.1% (v/v) of formic acid) and (B) acetonitrile (0.1% (v/v) of formic acid) with the following gradient: 0-1.10 min 5% (v/v) of B and 95% (v/v) of B at 6.40 min. The flow rate was set at 400 μL·min−1. Solvent and analytes were ionized with an electrospray (Nebulizer pressure=2 bars and nitrogen dry gas flow=10 L·min-1). Ions transfer was done with an end plate offset at 500 V and transfer capillary voltage at 4,500 V. A divert valve was used to inject four times diluted ESI-L Low Concentration Tuning Mix (Agilent, Les Ulis, France) at the beginning of each run, allowing a recalibration of each spectrum. The mass spectrometer was calibrated with undiluted Tuning Mix before batch analysis in enhanced quadratic mode, with less than 0.5 ppm errors after calibration. Analyses were done in two mass ranges: between 100 to 1,500 m/z and between 1,500 to 3,000 m/z, both in negative and positive ionization modes. Quality control was used to guarantee the stability of the LC-MS system before each sample run. Features (aligned m/z-values and retention time) fragmentation was performed using the AutoMSMS function on the most intense features with a frequency of 2 Hz. The fragmentation was done at 3 different collision energies: 15, 25 and 35 eV. Parent ions and fragments were submitted to different databases (notably thanks to the massTRIX interface (http://masstrix.org) (Suhre & Schmitt-Kopplin, 2008) and YMDB 2.0 (http://www.ymdb.ca) (Ramirez-Gaona et al., 2017)) and both compositional (obtained from FT-ICR-MS) and structural information have been used to identify compounds with high confidence level.

FT-ICR-MS—Metabolomics Analyses by Fourier Transform Ion Cyclotron Resonance Mass Spectrometry Ultra-high-resolution mass spectra were acquired in negative mode on a Bruker SolariX Ion Cyclotron Resonance Fourier Transform Mass Spectrometer ((−)FT-ICR-MS) (BrukerDaltonics GmbH, Bremen, Germany) equipped with a 12 Tesla superconducting magnet (Magnex Scientific Inc., Yarnton, GB) and a APOLO II ESI source (BrukerDaltonics GmbH, Bremen, Germany), and operating in negative and positive ionization modes. 20 µL of sample were diluted in 1 mL of pure methanol and then injected at a flow rate of 120 µL/h into the microelectrospray. Spectra were acquired with a time-domain of 4 mega words over a mass range of m/z 147 to 2000. A total of 300 scans were accumulated for each sample. All samples were injected randomly in the same batch to avoid batch variability. External calibration was done with clusters of arginine (10 mg/L in methanol). Internal calibration was performed for each sample by using yeast ubiquitous compounds for negative mode (Gougeon et al., 2009)(Supplementary information 2). External and internal calibration led to a day-to-day mass accuracy lower than 0.1 ppm.

Identification of Metabolites by Liquid Chromatography Coupled to Time-of-Flight Mass Spectrometry The separation was done with an ultra-high-pressure liquid chromatography (Dionex Ultimate 3000, ThermoFischer) coupled to a MaXis plus MQ ESI-Q-TOF mass spectrometer (Bruker, Bremen, Germany). The non-polar and low polar metabolites were separated in reversed phase liquid chromatography (RP-LC) by injecting 5 µL in an Acquity UPLC BEH C18 1.7 µm column 100×2.1 mm (Waters, Guyancourt, France). Elution was performed at 40° C. by (A) acidified water with 0.1% (v/v) of formic acid and (B) acetonitrile with 0.1% (v/v) of formic acid with the following gradient: 0-1.10 min 5% (v/v) of B and 95% (v/v) of B at 6.40 min. The flow rate was set at 400 µL/min and kept 5 min with initial condition before each injection. Solvent and analytes were ionized with an electrospray (Nebulizer pressure=2 bars and nitrogen dry gas flow=10 L/min). Ions transfer was done with an end plate offset at 500 V and transfer capillary voltage at 4500 V. A divert valve was used to inject four times diluted ESI-L Low Concentration Tuning Mix (Agilent, Les Ulis, France) at the beginning of each run, allowing a recalibration of each spectrum. The mass spectrometer was calibrated with undiluted Tuning Mix before batch analysis in enhanced quadratic mode, with less than 0.5 ppm errors after calibration. Spectra were acquired on the 100 to 1500 m/z mass range, both in negative and positive ionization modes. MS quality control (mix of standard peptides and polyphenols) and experimental quality control (mix of samples) were used to guarantee the LC-MS system performance. All samples were injected randomly in the same batch to avoid batch-to-batch variability. Features (couple of m/z-values and retention times) fragmentation was performed using the AutoMSMS function on the most intense features with a frequency of 2 Hz. The fragmentation was done at three different collision energies: 15, 25 and 35 eV.

Data Analysis

Results were expressed as the average of three replicates with the associated standard deviations.

(−)FT-ICR-MS data were handled with DataAnalysis (v. 4.3, Bruker Daltonik GmbH). Calibrated data were filtered to keep only m/z peaks with a signal to noise (S/N) ratio above 10 and an absolute intensity higher than 2.0×106. Peaks alignment was made by Matrix Generator software (v. 0.4, Helmholtz-Zentrum Muenchen) with a mass accuracy window of 1 ppm (Lucio, 2009). Peaks with intensity equal to 0 in more than 80% of samples were removed from the analysis. Finally, the homemade software NetCalc 2015 (v. 1.1a, Helmholtz-Zentrum Muenchen) was used to annotate peaks (Tziotis et al., 2011). 46% of the initially aligned peaks were annotated by NetCalc and used for this study. Van Krevelen diagrams, which plot the H/C against the 0/C ratio of annotated metabolites were generated by a homemade excel file, providing instantaneous chemical pictures of the metabolites diversity (Brockman et al., 2018; Kim et al., 2003). The OligoNet webserver was also used to annotate potential peptides with a max error of 1 ppm (Liu et al., 2017).

The LC-Q-ToF-MS data were calibrated internally by 1/4 diluted tuning mix. Calibrated features were filtered by S/N better than 30 and an absolute intensity of at least 1,000. Before features extraction, the spectral background noise was removed. The extracted features were aligned with a homemade R software with an m/z tolerance of 2 ppm and retention time tolerance of 0.2 seconds. Parent ions and fragments were submitted to different databases with the MassTRIX interface (http://masstrix.org) (Suhre & Schmitt-Kopplin, 2008), Metlin (https://metlin.scripps.edu) and YMDB 2.0 (http://www.ymdb.ca) (Ramirez-Gaona et al., 2017). According to the precision of LC-Q-ToF-MS and (−) FT-ICR-MS, an error of 3 ppm and 1 ppm was chosen respectively for the annotation of the metabolites (Roullier-Gall et al., 2014; Roullier-gall et al., 2015). The combination of these databases allows covering a wide range of metabolites found in biological systems, and notably in yeast.

Results and Discussion

Macromolecular Analysis

Figure 5:
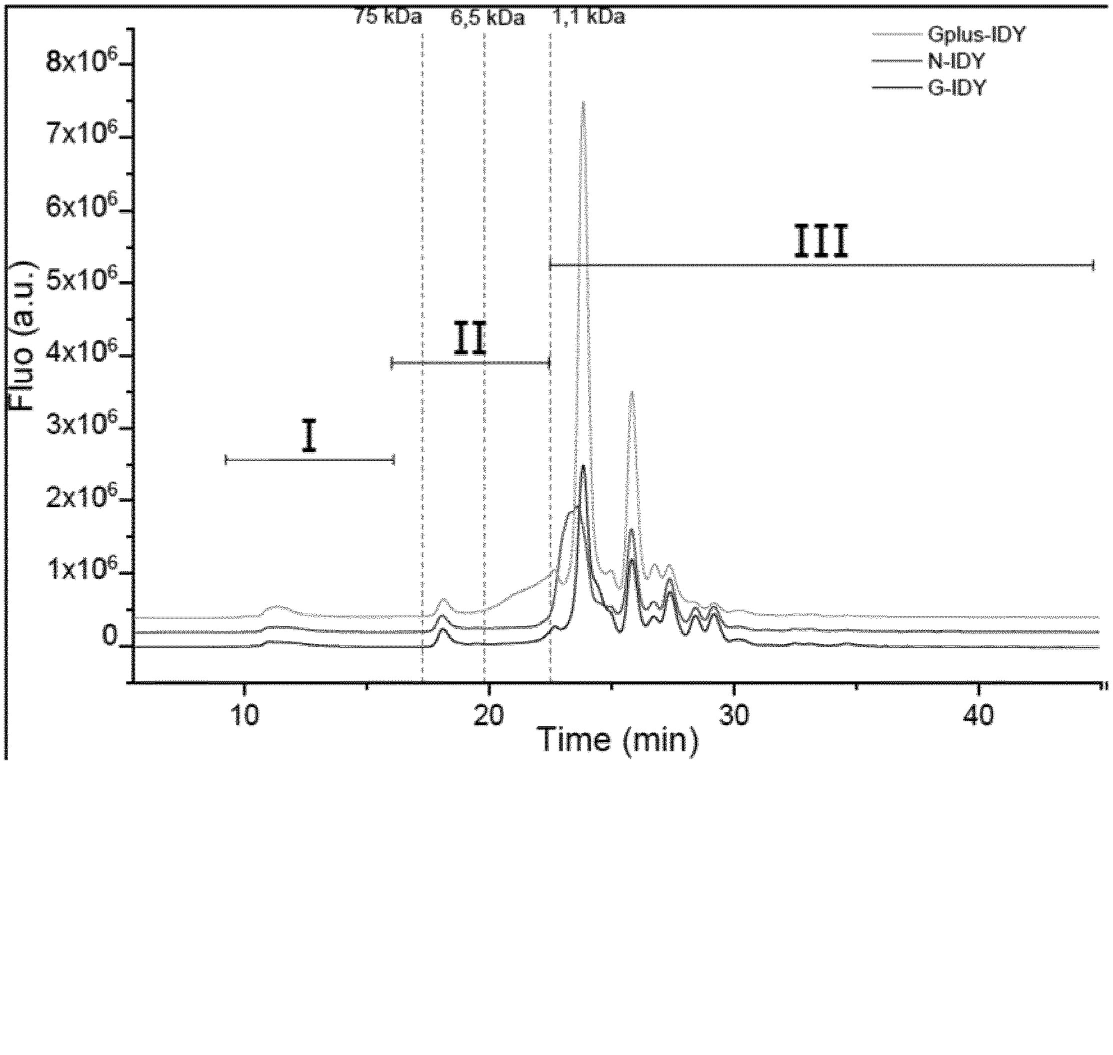
FIG. 5 illustrates Gel Permeation Chromatograms of Model Wine Soluble Fraction (MWSF) for G-IDY (bottom line in dark grey), Gplus-IDY (top-most line in light grey) and N-IDY (middle line in mid-grey).

Besides the obvious discrimination between soluble and not soluble fractions in a specific medium, the gel permeation chromatography is dedicated to determine the global size repartition of compounds within complex samples. This first experiment appeared as a good introduction to the relatively unknown diversity of compounds released by IDY in different extraction media. Acidified water and model wine were chosen to be representative of what can be released by IDY in must and wine, respectively. Methanol is used to have an overview of the mildly hydrophobic soluble fraction present in our samples, independently of the oenological conditions in winemaking process. In this example, it was possible to separate macromolecules from 200,000 Da to 5,000 Da between 9.5 min and 22.5 min according to the column specification. Separation was performed with model wine and without any denaturant to keep macromolecules in their native forms. The fluorescent detector was set up to track the presence of potent proteinaceous fluorophores among the chromophoric material extracted from yeast extracts (Coelho et al., 2017). FIG. 5 shows GPC chromatograms of MWSF for G-IDY, Gplus-IDY and N-IDY. These chromatograms clearly revealed three different time lap windows common to all MWSF extracts. The first time frame (I) between 9.5 and 17.3 min represents about 1% of the total fluorescent response and had a mass range from 200 to 75 kDa. G-IDY, Gplus-IDY and N-IDY showed no significant difference in composition of high molecular weight molecules from 200 to 75 kDa. This result is in accordance with Pozo-Bayon and collaborators (2009), who reported that high molecular weight compounds are in lower concentration than peptides and amino acids in the model wine soluble fraction in different IDY (Pozo-Bayón et al., 2009). In these conditions, the percentage of high molecular weight compounds released from G-IDY, Gplus-IDY and N-IDY was always low, whatever the solvent used (not shown). However, methanol extracts showed limited high molecular weight responses because of precipitation (Chertov et al., 2004).

The second time frame window (II) in the chromatogram, between 17.3 and 22.5 min, represents medium molecular weight compounds in a mass range from 75 to 5 kDa the exclusion limit of the column. G-IDY, Gplus-IDY and N-IDY relative concentrations in medium molecular weight compounds varied from 7 to 14% compared to the total, in an extraction medium dependent manner. In detail, WSF and MWSF extraction media for Gplus-IDY presented 1.5-fold higher medium molecular weight compounds concentration compared to those for G-IDY and N-IDY. However, MSF presented relatively low concentrations of medium molecular weight compounds, of about 3% of the total fluorescence responses (not shown).

Finally, the most abundant fluorescent responses (whatever the extraction media) were observed for the third time-frame (III) from 22.5 to 45 min, where fluorescent compounds accounted for 92%, 91% and 86% of the total fluorescence response of G-IDY, N-IDY, and Gplus-IDY respectively in model wine extraction medium.

In addition, in order to get a more representative characterization of IDY soluble fractions, UV detection at 210 nm was also considered. UV detection is less sensitive and less specific to one chemical function compared to fluorescence and allows the peptide bond, carbon to carbon and carbon to oxygen double bond detection (Stoscheck, 1990).

On the basis of these results, and whatever the detection method or the extraction medium used, GPC could not discriminate IDY soluble fractions. The medium and high molecular weight compounds showed a similar fluorescent profile among samples which indicated that the bio-process enrichment would only impact the low molecular weight fraction of IDYs. In that respect, to go further on the characterization of IDY soluble fractions, ultra-high-resolution mass spectrometry was used to assess the diversity of the abundant low molecular weight compounds.

IDY Low Molecular Weight Chemical Diversity

Figure 6A:
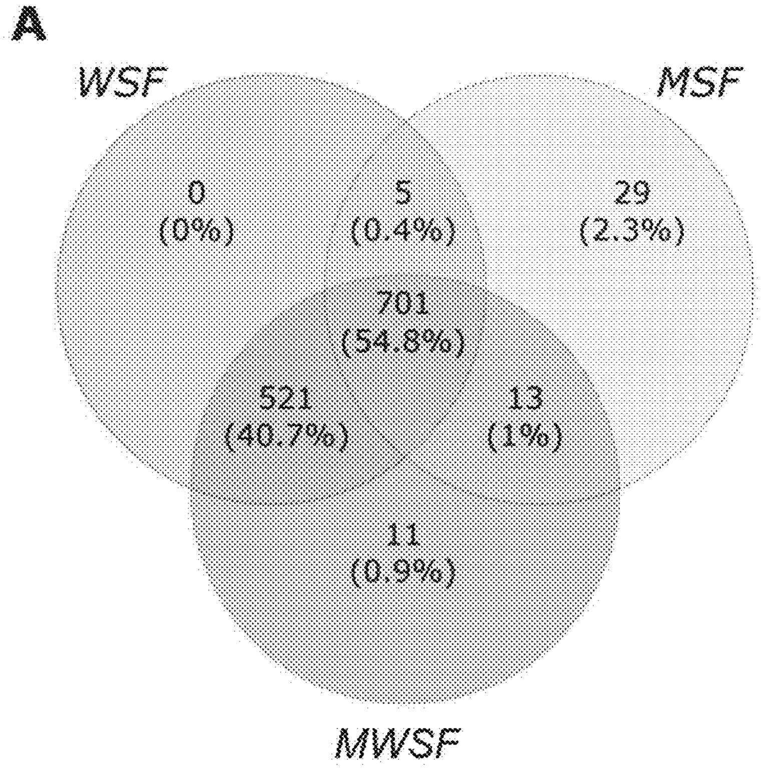
FIG. 6A illustrates the number of ions found in the different extraction media for a given soluble fraction (G-IDY).

The ultra-high accuracy of FT-ICR-MS enables to obtain the exact mass of ionizable compounds present in complex matrices including wine (Roullier-Gall et al., 2017; Roullier-Gall, Witting, Gougeon, & Schmitt-Kopplin, 2014) thus allowing to have access to a more comprehensive chemical diversity present in the sample. FIG. 6A gives an overview of the number of ions found in the different extraction media for a given soluble fraction (G-IDY). Of the 1674 ions detected for G-IDY, 701 (54.8%) were common to all extraction media and only 40 (3.2%) were found to be specific to extraction media. MWSF showed the best extraction yield with 97.4% of the total extractable m/z ions (N-IDY and Gplus-IDY MWSF have similar extraction yield with 85.4% and 89% respectively, data not shown). The medium polarity of model wine led to a better solubilization of IDY compounds than water and methanol alone. Based on this result, G-IDY, Gplus-IDY and N-IDY MWSFs were compared in order to characterise the diversity of IDY extractible compounds. For all conditions, yeast derivatives were inactivated by short term heating before being dried and sealed hermetically for storage. In that respect, compounds potentially released by IDY are a combination of bio-accumulated metabolites and bio-transformed compounds related to the production process. Since the inactivation and drying process were identical for the three IDYs, it can be assumed that the major contribution to the observed diversity could be mainly attributed to the bio-process.

Figure 6B:
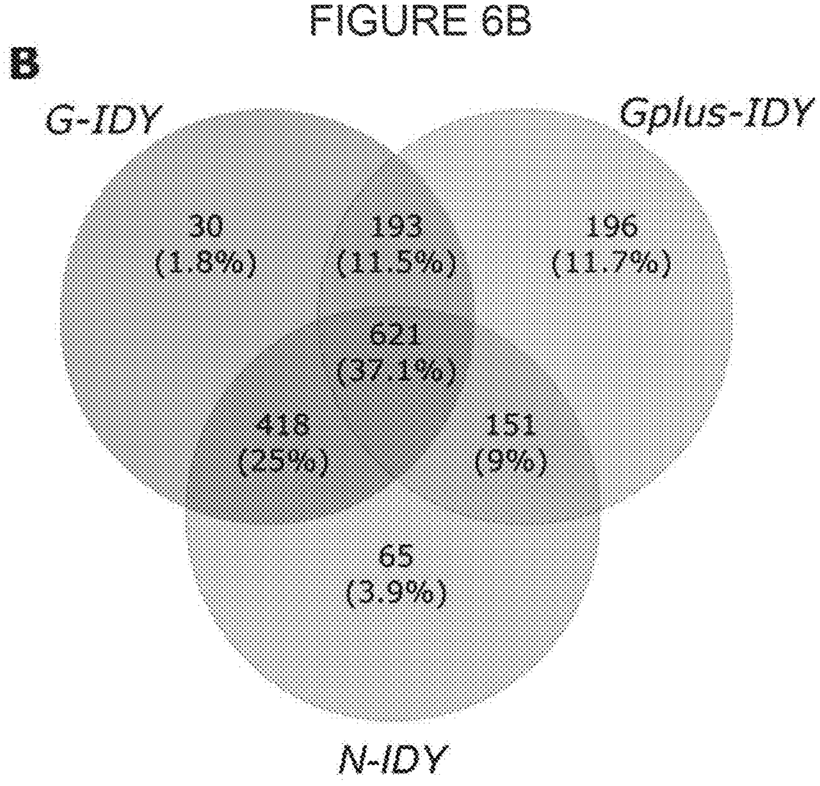
FIG. 6B illustrates the model wine extractable ions common to each IDY and the number of ions unique to G-IDY, N-IDY and Gplus-IDY, respectively.

As presented in FIG. 6B, 37.1% of the total extractable ions were common to each IDY and only 1.8%, 3.9% and 11.7% of the ions were unique to G-IDY, N-IDY and Gplus-IDY, respectively. We also observed that N-IDY and G-IDY, obtained from the same yeast strain, shared more common ions (62.1%) than with Gplus-IDY (46.1% and 48.6% respectively). These results show that both the intracellular accumulation of glutathione and the yeast strain are key factors modifying the metabolic signatures of IDY soluble fractions, in agreement with existing literature (Allen et al., 2003; Brauer et al., 2006; Dikicioglu, Dunn, Kell, Kirdar, & Oliver, 2012).

Figure 7E:
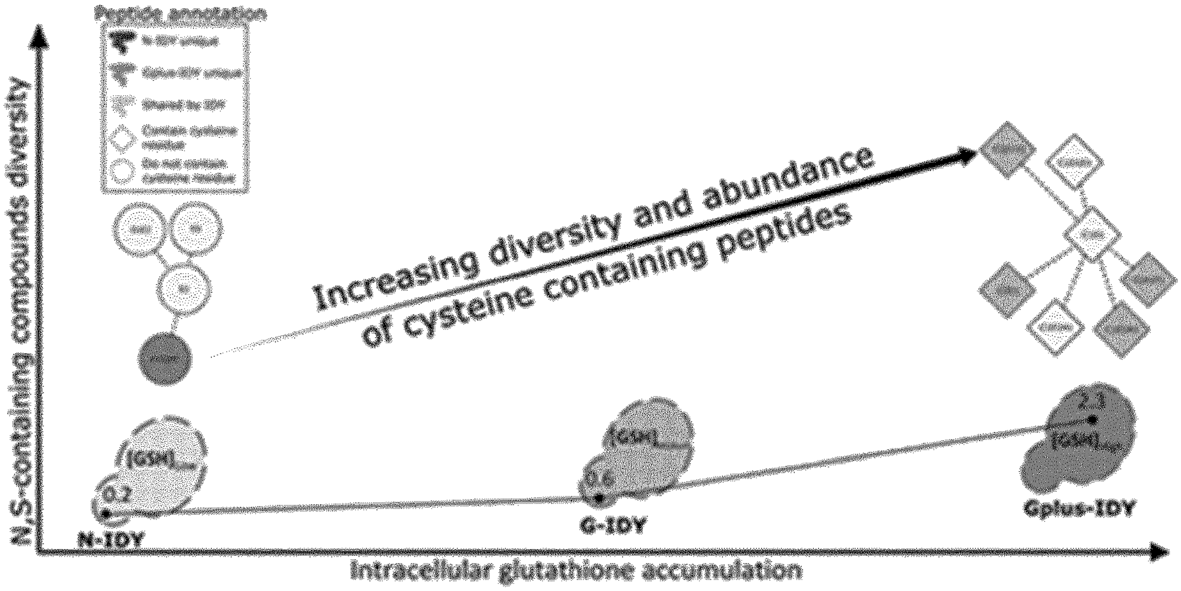
FIG. 7E illustrates the accumulation of intracellular glutathione in N-IDY, G-IDY and the Gplus-IDY, with G-IDY releasing 3 times more CHONS compounds than N-IDY, and G-plus-IDY releasing more than 10 times more compounds than N-IDY.

Network annotation of the m/z ions present in MWSF (which is the solvent with the better extraction yield for all IDY according to 3.2) allow to have access to the molecular formulas of 53% of the initial ions. The extensive chemical differences between G-IDY, Gplus-IDY and N-IDY MWSFs were clearly visible from the histograms depicting the distribution of elemental compositions (CHO, CHON, CHOS, and CHONS), along with van Krevelen diagrams and m/z-resolved H/C atomic ratios of the (−)ESI FT-ICR-MS derived molecular formulas (FIGS. 7A to E). Up to 888 m/z ions were annotated by NetCalc amongst the 1674 aligned masses from MWSFs. FIG. 3A presents the 379 annotated m/z ions common to the three IDYs soluble fractions in model wine (MWSF). These ions could be considered as representative of extractable metabolites from IDYs whatever the strain or the production process. Common ions were found in different chemical spaces such as lipid-like, peptide-like and saccharide-like domains, which agrees with a glutathione accumulation bioprocess that preserves the yeast basic metabolism during the production FIGS. 7B, 7C and 7D show annotated masses unique to each MWSFs, colored according to their chemical compositions. A first overview of the Van Krevelen diagrams reveals significant differences between the samples in terms of number of unique formulas (already visible in FIGS. 2A and B) and chemical families. N-IDY (FIG. 7D) appeared much richer in unique CHO containing formulas (16) than G-IDY (3) and Gplus-IDY (0). These formulas are mainly in peptide-like and lipid-like domains, which could correspond to small chain fatty acids or saccharides for example. In contrast, Gplus-IDY (FIG. 7B) was characterized by a significantly higher number of unique CHONS containing formulas compared to G-IDY and N-IDY (36 against 3 and 1, respectively). These formulas, mainly located in the peptide-like domain could correspond to peptides with sulfur-containing amino acid residues, such as methionine and cysteine. The high diversity of thiol containing compounds (—SH group) could explain the relative activity of these products against oxidation as it is known than peptides and thiols could have antioxidant property in wine (Elias et al., 2008; Nikolantonaki, Chichuc, Teissedre, & Darriet, 2010; Nikolantonaki, Magiatis, & Waterhouse, 2014). It is remarkable to note how the glutathione enrichment process, which is designed to accumulate intracellular glutathione, is actually accompanied by an overall increase of the CHONS/CHO ratio when going from N-IDY to Gplus-IDY (FIG. 7E), with G-IDY releasing 3 times more CHONS compounds than N-IDY, and G-plus-IDY releasing more than 10 times more compounds than N-IDY. With a moderate hypothesis of 3 isomers per FT-ICR-MS peak, these results show altogether that Gplus-IDYs would be discriminated by more than 100 different N,S-containing compounds, compared to G-IDY and N-IDY, thus providing an unprecedented molecular representation of the actual metabolic response of glutathione enrichment. The relatively low number of unique compounds released from G-IDY is not surprising since it is obtained from the same strain as N-IDY, and it follows the same bio-process than Gplus-IDY thus most of the released compounds are likely shared with at least one other IDY.

Impact of GSH Enrichment Process on IDYs Peptides Diversity

Figure 4A:
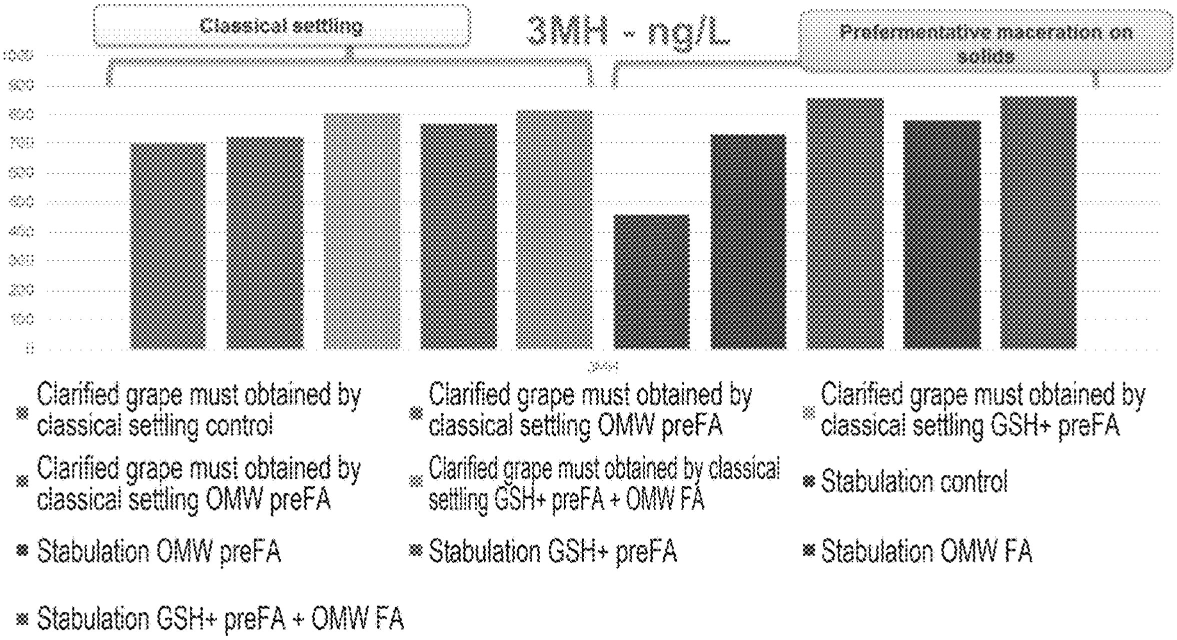
FIGS. 4A, 4B, 4C and 4D illustrate the impact of the rich-glutathione inactivated yeast in accordance with the present description (GPlus inactivated yeast) on three major volatile varietal thiols levels (3MH, 3MHA and 4MMP) after bottling. Left to right the columns are as follows: (1) Clarif témoin; (2) Clarif OMW preFA; (3) Clarif GSH+preFA; (4) Clairf OMW FA; (5) Clarif GSH+preFA+OMW FA; (6) Stabu témoin; (7) Stabu OMW preFA; (8) Stabu GSH+preFA; (9) Stabu OMW FA; and (10) Stabu GSH+preFA+OMW FA.
Figure 4B:
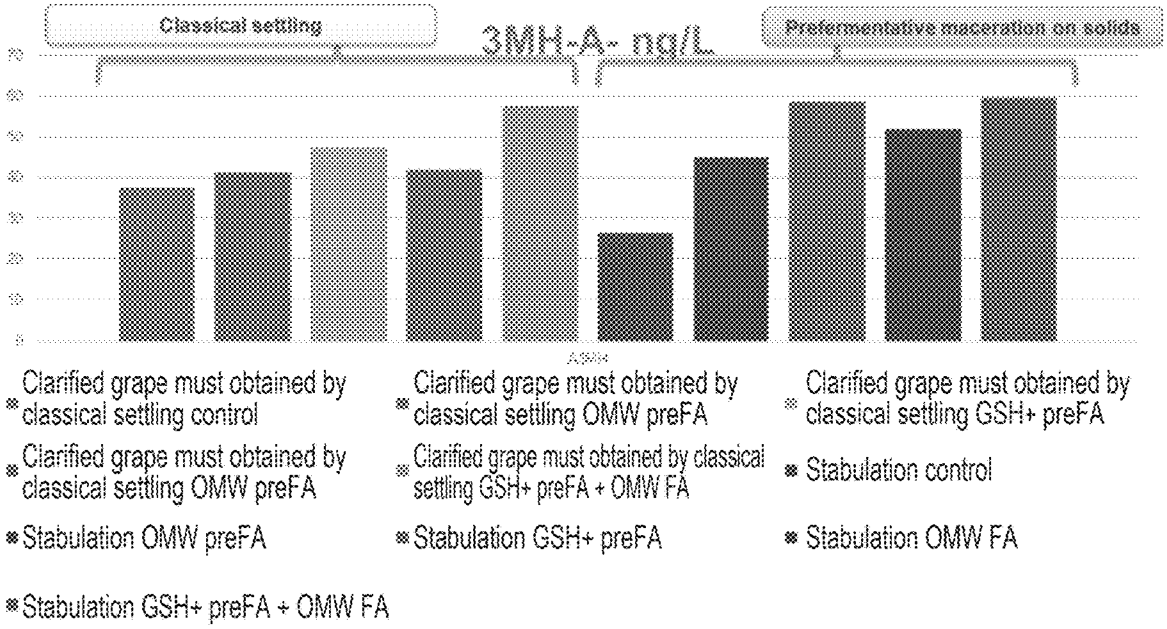
Figure 4C:
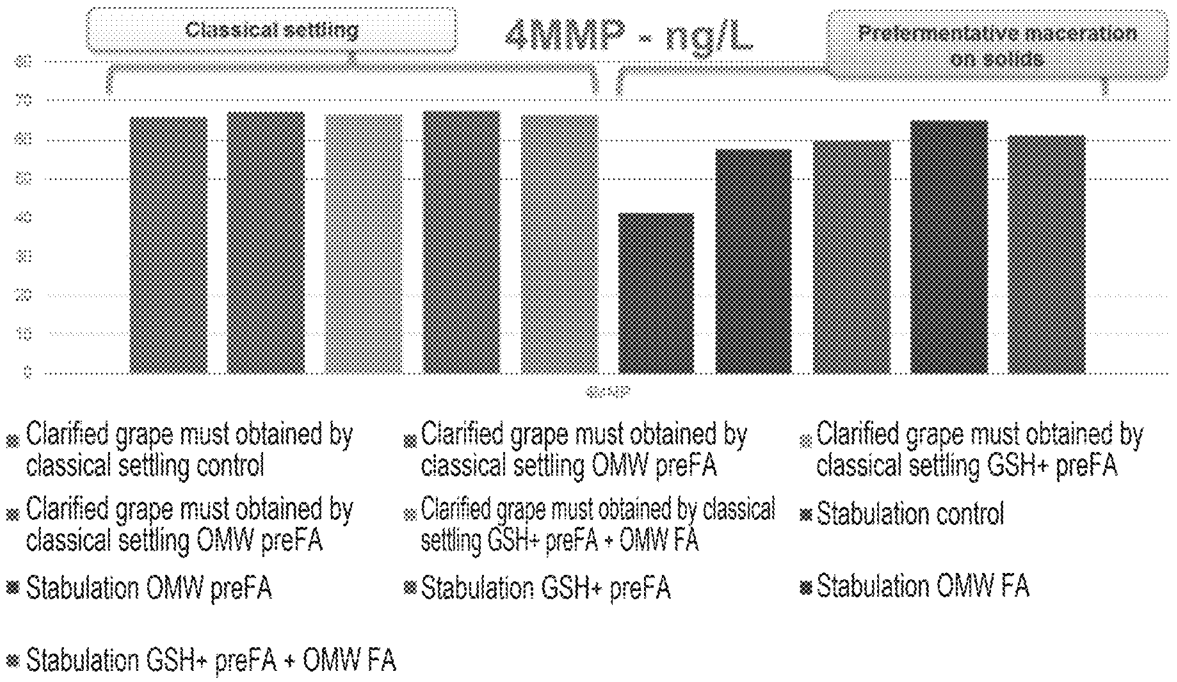
Figure 4D:
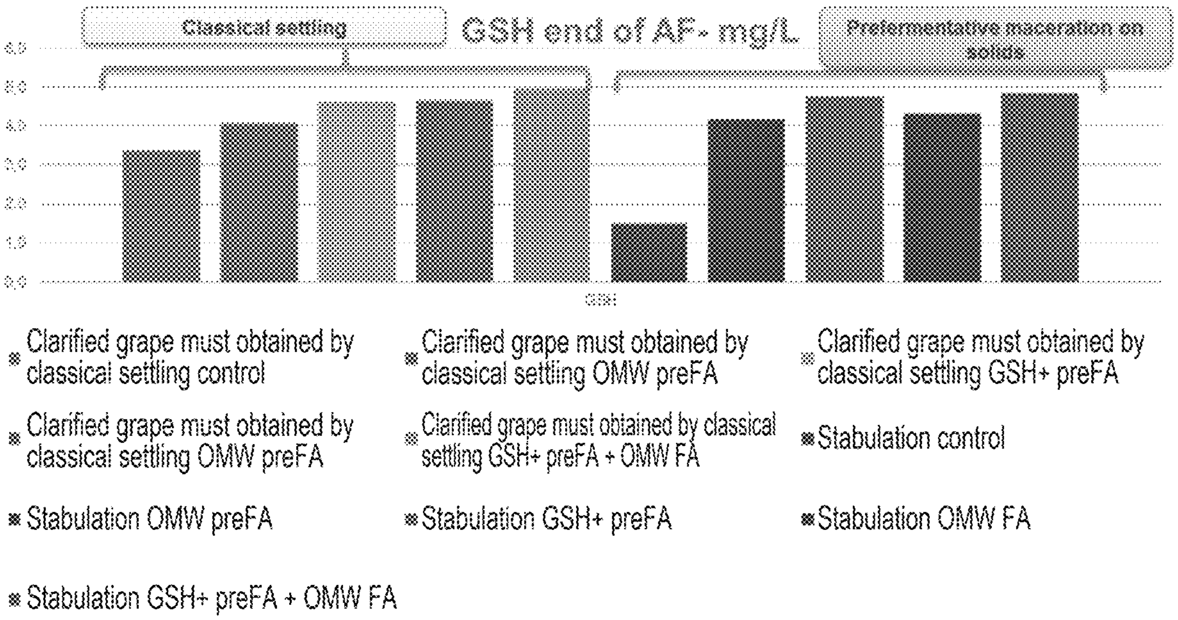
Figures 8A, 8B, 8C:
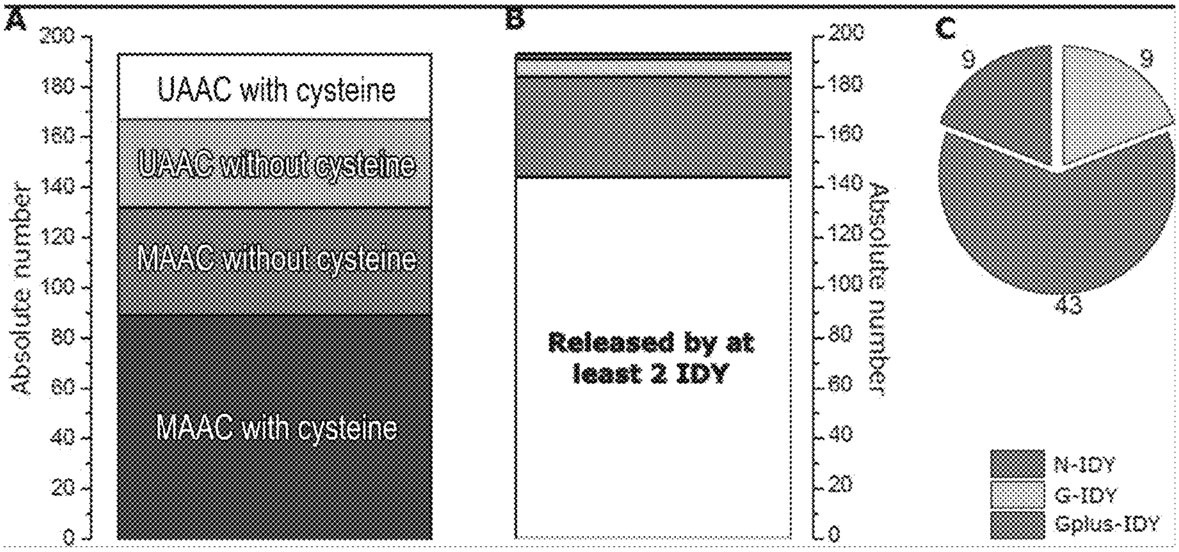
FIGS. 8A, 8B and 8C illustrate the great diversity of peptides (40) present in Gplus-IDY against 7 and 2 for G-IDY and N-IDY, respectively.

The presence of cysteine into the growth medium during IDY GSH enrichment processing in industrial scale (Li et al., 2004), modify the global metabolism of sulfur amino acids and leads to over representation of sulfur-containing metabolites (Thomas & Surdin-Kerjan, 1997). Since the Van Krevelen diagrams pointed out the increasing diversity of CHON and CHONS containing compounds along with the enrichment process, this diversity could be putatively attributed to peptides containing cysteine or methionine residues. Amongst the 1674 m/z submitted to the OligoNet webserver, 193 were annotated as potential peptides (from 2 to 5 residues) with an error below 1 ppm (Supplementary information 4). Within the 193 annotated ions, 132 have a Multiple Amino Acids Combination (MAAC) and 61 a Unique Amino Acids Combination (UAAC) (FIG. 4A). Most of the peptides (144 m/z) are common to at least two out of three IDYs, whereas Gplus-IDY presents the greatest diversity with 40 peptides against 7 and 2 for G-IDY and N-IDY, respectively (FIG. 8B). Amongst the UAAC, 26 out of 65 contain a cysteinyl residue. These unambiguous annotations of peptides allowed to draw all possible connections between these peptides (Supplementary information 5). The Gplus-IDY clearly released more unique peptides and more peptides with a cysteinyl residue. Nevertheless, most of the UAAC are shared between the IDYs (regardless of their relative concentrations). The global similarity between our samples analyzed by (−)FT-ICR-MS allowed to compare the absolute intensity between samples giving an idea of the abundance of each compound released. FIG. 4C reveals that within the 61 UAAC released by the IDY, Gplus-IDY released 28 peptides significantly more intense than G- and N-IDY (3 peptides and 1 peptides respectively). These results are in accordance with the Van Krevelen diagram (FIG. 7B) showing a higher diversity of compounds in the peptide-like domain for Gplus-IDY.

FT-ICR-MS enables to have access to the elemental formulas of detected ions and thus to get instantaneous metabolic fingerprints of what is released by IDY. Since a single CHONS elemental formula can be associated with numerous compounds, (especially for high m/z ions) the combination with separative LC-MS and LC-MS/MS methods was used to access structural and quantitative information about these molecular markers (Roullier-Gall et al., 2014). FIG. 8A shows a visual overlaid of FT-ICR-MS spectrum and LC-MS spectrum of the G-IDY MWSF, in the 295-330 m/z mass range. The highest resolution of the (−)FT-ICR-MS (600,000 against 20,000 for LC-MS at m/z 306) was used to annotate LC-MS peaks which could be aligned with (−)FT-ICR-MS peaks, using a homemade alignment script. Up to 128 m/z peaks of the (−)LC-MS spectra where found to match (−)FT-ICR-MS peaks (with an absolute error lower than 2 ppm). Alignment was done on the basis of the similarity of m/z without consideration of the retention time, only for the negative mode of the LC-MS. The aim was to have both an unambiguous annotation of (−)LC-Q-ToF-MS ions with the ultrahigh resolution of (−)FT-ICR-MS, and a quantitative information from LC-Q-ToF-MS. Ions present in (−)LC-Q-ToF-MS data but not found in (−)FT-ICR-MS data (FIG. 8B) were likely molecules easily suppressed in direct infusion with ESI, showing the added value of using chromatographic separation before MS analysis (Roullier-Gall et al., 2014).

Keeping in mind the formula annotation of m/z ions with the FT-ICR-MS data, the fragmentation of 16 features (in positive and negative ionization mode) enabled to have access to the putative structure of corresponding compounds. Fragments were submitted to metabolomic databases, and results matching with the FT-ICR-MS annotation of the parent's ions are summarized in Table 1. Following the new prescriptions of Sumner and collaborators, the identification point (giving the identification confidence) of each metabolite is 5.5 (High resolution retention time, accurate mass of parent ion, molecular formula based upon accurate m/z and isotope pattern and accurate tandem mass spectrum) (Sumner et al., 2014). Most of these compounds were already described in yeast as metabolite pathways, but never so far as released compounds from IDY. Most interestingly, glutathione and its precursor (glutamyl-cysteine) were found in the three extracts, but consistently with the enrichment process, i.e. with a relative abundance following the Gplus>G>N trend. In contrast, lysine-leucine and arginine-leucine dipeptides appeared as GPlus-IDY markers, whereas homocitric acid appeared as N-IDY marker. Amino acids (glutamate, tyrosine, phenylalanine), which have been extensively studied in IDY (Pozo-Bayon et al., 2009) were examples of contrasted trends with relative concentrations that did not appear to be directly correlated to the enrichment process, since they could have a positive impact as yeast assimilable nitrogen source in N-deficient musts, and help sluggish alcoholic fermentation. Similarly, methyl-thioadenosine, a precursors of adenosylmethionine is a sulfur and nitrogen stock molecule in poor medium (Shapiro & Schlenk, 1980), and thus a potential fermentation enhancer already putatively annotated in IDY (Rodriguez-Bencomo et al., 2014). Weak organic acids like citric acid have been described for their sensory impact (fresh notes), whereas homocitric acid and pipecolic are related to the lysine metabolism in yeast (He, 2006; Tucci & Ceci, 1972), but not described in IDY yet. Finally, the pantothenic acid showed a promoting effect on yeast growth (Richards, 1936) is much more present in N-IDY than in G-IDY and Gplus-IDY. Adenosine and arginine-leucine were recently shown to possibly promote bacteria growth (Liu et al., 2016, 2017) and thus help the malolactic fermentation. Whereas Adenosine are abundant in the thress IDY, the dipeptide Arg-Leu is specific to Gplus-IDY and almost absent in the other IDY. Such structural identifications provide a good overview of the richness and the diversity of compounds released by IDY, and it also highlights the yet unknown contribution of IDYs.

TABLE 1

Metabolites fragmented by LC-Q-ToF-MS/MS in the MWSF for the three IDYs, and their corresponding chemical family

| m/z Adduct | Ret. time (min) | Collision energy (eV) | Discriminant Fragments | Annotation [M] | Error (ppm) | Area (%) N-IDY | G-IDY | Gplus-IDY | Identified metabolite | Database ID |
|---|---|---|---|---|---|---|---|---|---|---|
| 130.0863 [M + H]+ | 0.7 | 30 | 84.0808 | $C_6H_{11}NO_2$ | 0.35 | 100 | 43 | 41 | Pipecolic acid | C00408 (KEGG) |

TABLE 1-continued

Metabolites fragmented by LC-Q-ToF-MS/MS in the MWSF for the three IDYs, and their corresponding chemical family

| m/z Adduct | Ret. time (min) | Collision energy (eV) | Discriminant Fragments | Annotation [M] | Error (ppm) | Area (%) N-IDY | Area (%) G-IDY | Area (%) Gplus-IDY | Identified metabolite | Database ID |
|---|---|---|---|---|---|---|---|---|---|---|
| 148.0601 [M + H]+ | 0.6 | 15 | 84.0447; 130.0497 | $C_5H_9NO_4$ | −2.03 | 100 | 78 | 53 | Glutamic acid | C00025 (KEGG) |
| 165.0548 [M + H]+ | 0.7 | 10 | 147.0442; 119.0492; 91.0544 | $C_9H_8O_3$ | 1.08 | 47 | 30 | 100 | Coumaric acid | C12621/ C00811 (KEGG) |
| 166.0861 [M + H]+ | 1.0 | 15 | 166.0862; 120.0806; 131.0490 | $C_9H_{11}NO_2$ | −1.20 | 44 | 36 | 100 | Phenylalanine | C00079 (KEGG) |
| 179.0485 [M + H]+ | 0.7 | 10 | 162.0222; 144.0116; 116.0164 | $C_5H_{10}N_2O_3S$ | 0.06 | 36 | 91 | 100 | Cysteinyl-glycine | C01419 (KEGG) |
| 182.0811 [M + H]+ | 0.7 | 15 | 136.0757; 123.0438; 147.0442 | $C_9H_{11}NO_3$ | −0.55 | 71 | 43 | 100 | Tyrosine | C00082 (KEGG) |
| 191.0199 [M − H]− | 0.7 | 15 | 173.0095; 129.0197; 111.0094 | $C_6H_8O_7$ | 1.05 | 100 | 37 | 17 | Citric acid | C00158 (KEGG) |
| 205.0355 [M − H]− | 0.8 | 15 | 143.0352; 125.0248 | $C_7H_{10}O_7$ | 0.49 | 100 | <1 | <1 | Homocitric acid | C05662 (KEGG) |
| 218.1037 [M − H]− | 1.1 | 15 | 146.082 | $C_9H_{17}NO_5$ | 1.38 | 100 | 63 | 73 | Pantothenic acid | C00864 (KEGG) |
| 251.0693 [M + H]+ | 0.7 | 15 | 122.0269; 130.0497; 188.0373 | $C_8H_{14}N_2O_5S$ | −1.19 | 19 | 71 | 100 | Glutamyl-cysteine | C00669 (KEGG) |
| 258.11 [M + H]+ | 0.6 | 20 | 184.0735; 104.1070 | $C_8H_{20}NO_6P$ | −0.39 | 18 | 23 | 100 | Glycerophosphocholine | C00670 (KEGG) |
| 260.1969 [M + H]+ | 0.8 | 30 | 147.1132; 129.1025; 84.0810 | $C_{12}H_{25}N_3O_3$ | 0.12 | <1 | <1 | 100 | Leucyl-lysine | HMDB28912 (HMDB) |
| 268.1037 [M + H]+ | 0.7 | 15 | 119.0353; 136.0617 | $C_{10}H_{13}N_5O_4$ | −1.12 | 92 | 100 | 94 | Adenosine | C00212 (KEGG) |
| 288.2030 [M + H]+ | 0.8 | 20 | 271.1763; 175.1187 | $C_{12}H_{25}N_5O_3$ | −0.06 | <1 | <1 | 100 | Leucyl-arginine | HMDB28923 (HMDB) |
| 298.0970 [M + H]+ | 1.3 | 15 | 136.0616; 145.0320 | $C_{11}H_{15}N_5O_3S$ | 0.67 | 74 | 100 | 85 | Methyl-thioadenosine | C00170 (KEGG) |
| 306.0763 [M − H]− | 0.7 | 15 | 272.0890; 143.0464; 210.0882 | $C_{10}H_{17}N_3O_6S$ | −0.65 | 33 | 89 | 100 | Glutathione | C00051 (KEGG) |

In this example, the model wine soluble fractions of three inactivated dry yeasts were characterized by a combination of Gel Permeation chromatography (GPC), FT-ICR-MS and LC-Q-Tof-MS in order to provide a comprehensive picture of the diversity of potentially active compounds associated with the glutathione enrichment process. To that purpose, the extract of non-rich IDYs (N-IDY) was compared to extracts of a rich IDY from the same strain (G-IDY) and an even more rich IDY, but from a different strain (Gplus-IDY). GPC showed that most of the fluorescent compounds released by these IDYs have masses lower than 5 kDa. Consistently with the expected enrichment process, Gplus-IDY exhibited higher amounts of extractable glutathione (and its glutamyl-cysteine precursor) than G-IDY, which in turn appeared richer than N-IDY. However, lysine-leucine and arginine-leucine dipeptides appeared as examples of specific markers for Gplus-IDYs, whereas they were not detected in G-IDY and N-IDY. The metabolomic approach provided an unprecedented comprehensive molecular picture of the detailed impact of the glutathione enrichment process. It further revealed how the yeast strain can modulate the extent of the enrichment process, with the identification of more than hundred N,S-containing potential active compounds for Gplus-IDYs, most of them being unknown yet. Altogether, our results shed important light on the potential activity of IDYs on musts and wines, in terms of organoleptic and/or stability properties.

Example 6

In this example, the antioxidant properties of the glutathione-riche inactivated yeast of the present description were tested. The radical scavenging activity is a common and rapid way to investigate the antioxidant property of sample. In real wine, presence of dioxygen and iron leads to generate hydroxyl radical which could rapidly reacts with ethanol to produce ethyl radical. This radical react rapidly with radical scavenger in the solution such as nucleophilic compounds or antioxidant compounds.

The 2,2-diphenyl-1-picrylhydrazyl (DPPH) is a stable radical not naturally present in wine. The disappearance of DPPH radical leads to a decrease of absorbance at 525 nm. It is thus easy to see the amount of a specific compounds to decrease the initial absorbance of DPPH at 525 nm.

The DPPH assay was performed as followed in the following conditions:

A solution of 2,2-diphenyl-1-picrylhydrazyl (DPPH) was prepared by mixing 27 mg of DPPH with 1 L of 60:40 (v/v) 0.3 M buffer citrate-phosphate:methanol to reach a pH of 3.6.

Figure 9:
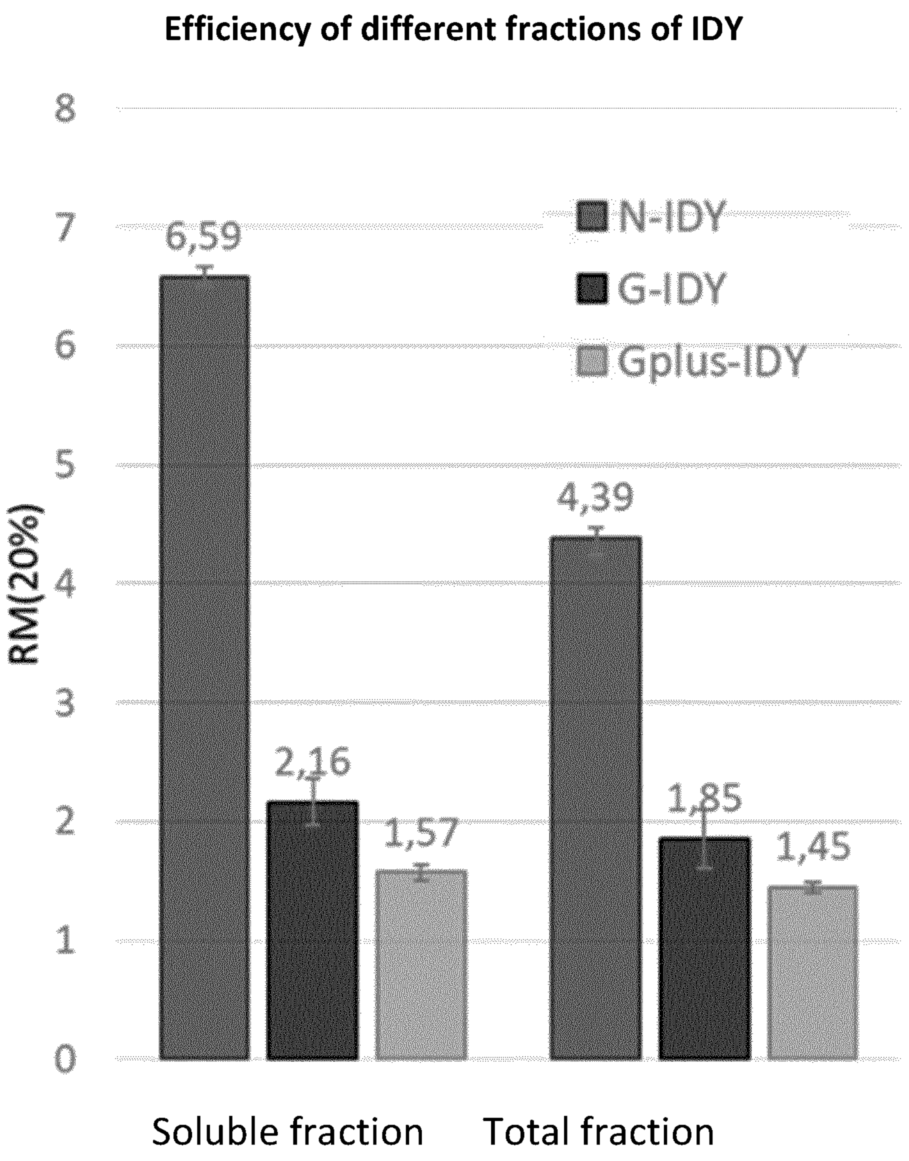
FIG. 9 illustrate the capacity of N-IDY, G-IDY and the Gplus-IDY (both total and soluble fractions sample) to scavenge 2,2-diphenyl-1-picrylhydrazyl (DPPH) radical.

3.9 mL of the DPPH solution was mixed with 0.1 mL of sample at different mass ratio YD/DPPH (Rm). The absorbance was read after 4 h into the dark at 525 nm with a UV-Visible spectrometer and normalized with the absorbance of a blank samples (buffer with 0.1 mL of model wine). The results were expressed as the Rm needed to reduce the initial absorbance of 20% noted Rm(20%). As seen on FIG. 9, the more the Rm(20%) value was low, more the IDY solution exhibited radical scavenging properties. FIG. 9 shows an estimation of the capacity of the 3 IDYs' (total and soluble fractions) to scavenge DPPH radical (by spectrophotometry). Radical-scavenging activity of the total and soluble fractions of the different IDYs can be classified in decreasing order of scavenging activities: Gplus-IDY>G-

IDY>N-IDY. Even though the insoluble fraction seemed to play a role in the radical scavenging action, the soluble fraction showed a greater scavenging activity.

The invention claimed is:

1. A must comprising an inactivated glutathione-rich *Saccharomyces cerevisiae* strain deposited at Institut Pasteur, on Feb. 20, 2019 under accession number CNCM I-5404.

2. The must of claim 1, wherein:

(a) the glutathione-rich *Saccharomyces cerevisiae* strain contains more than 0.5% of glutathione by weight relative to the weight of solids of the yeast; or (b) the glutathione-rich *Saccharomyces cerevisiae* strain contains at least 1% of glutathione.

3. The must of claim 2, wherein the glutathione-rich *Saccharomyces cerevisiae* strain contains at least 1.5% of glutathione by weight relative to the weight of solids of the yeast.

4. The must of claim 1, wherein the glutathione-rich *Saccharomyces cerevisiae* strain is in inactivated dry form, and wherein the inactivated dry form comprises a first dipeptide having the formula $C_{12}H_{25}N_3O_3$— with a molecular weight of 259.3458 g/mole; and a second dipeptide having the formula $C_{12}H_{25}N_5O_3$ with a molecular weight of 287.3593 g/mole.

5. The must of claim 4, wherein the first and second dipeptides are lysine-leucine and arginine-leucine dipeptides respectively, the lysine-leucine and arginine-leucine dipeptides are in an amount ranging from 0.0001-20 wt. %, based on a total weight of the inactivated glutathione-rich *Saccharomyces cerevisiae* strain.

6. The must of claim 1, wherein the glutathione-rich *Saccharomyces cerevisiae* strain is in inactivated dry form.

7. The must of claim 1, wherein the inactivated glutathione-rich *Saccharomyces cerevisiae* is present in an amount of 10 g to 100 g of solids per hectoliter of must.

8. The must of claim 1 wherein the must is a grape must.

9. The must of claim 8, wherein the grape must is for preparation of a wine, optionally a white wine.

10. A method for the prevention of defective ageing of white wine comprising, during the preparation of said wine, introducing glutathione-rich yeast into a must at the beginning of, during or after an alcoholic fermentation step, wherein the yeast is a *Saccharomyces cerevisiae* strain deposited at Institut Pasteur, on Feb. 20, 2019 under accession number CNCM I-5404.

11. The method as claimed in claim 10, wherein:

(a) the glutathione-rich yeast contains more than 0.5% of glutathione by weight relative to the weight of solids of the yeast; or (b) the glutathione-rich yeast contains at least 1% of glutathione, or at least 1.5% of glutathione, by weight relative to the weight of solids of the yeast.

12. The method as claimed in claim 10, wherein:

(a) the glutathione-rich yeast is introduced into the must in a proportion of 10 g to 100 g of solids per hectoliter of must, 20 g to 50 g of solids per hectoliter of must, or 20 g to 40 g of solids per hectoliter of must; or (b) the introduction of said glutathione-rich yeast into the must produces a provision of at least 0.5 mg of glutathione per liter of must, at least 1 mg of glutathione per liter of must, or approximately 2 mg of glutathione per liter of must.

13. The method as claimed in claim 10, wherein the glutathione-rich yeast is introduced into the must in one or more of the following forms: active dry yeast, inactivated dry yeast.

14. The method as claimed in claim 13, wherein the glutathione-rich yeast introduced into the must is a glutathione-rich yeast in inactivated dry yeast form.

15. The method as claimed in claim 14, wherein the introduction of the glutathione-rich yeast in inactivated dry yeast form into the must produces at least 2 mg of glutathione per liter of must, at least 4 mg of glutathione per liter of must, at least 8 mg of glutathione per liter of must, or at least 10 mg of glutathione per liter of must.

16. The method as claimed in claim 10, wherein the glutathione-rich yeast is at least part of the yeast inoculated into the must to carry out the alcoholic fermentation.

17. The method as claimed in claim 10, wherein yeast naturally containing glutathione is added to initiate the alcoholic fermentation.

18. The method of claim 10, wherein glutathione is released in the must during the fermentation or in the wine.

* * * * *